United States Patent
Ollila et al.

(10) Patent No.: US 10,272,264 B2
(45) Date of Patent: Apr. 30, 2019

(54) GENERATING TIME-EFFICIENT TREATMENT FIELD TRAJECTORIES FOR EXTERNAL-BEAM RADIATION TREATMENTS

(71) Applicant: Varian Medical Systems International AG, Cham (CH)

(72) Inventors: Santtu Ollila, Helsinki (FI); Mikko Vainio, Espoo (FI); Jarkko Peltola, Tuusula (FI); Janne Nord, Espoo (FI); Esa Kuusela, Espoo (FI); Juha Kauppinen, Espoo (FI); Viljo Petäjä, Espoo (FI); Marko Rusanen, Espoo (FI)

(73) Assignee: Varian Medical Systems International AG, Cham (CH)

( * ) Notice: Subject to any disclaimer, the term of this patent is extended or adjusted under 35 U.S.C. 154(b) by 262 days.

(21) Appl. No.: 15/269,870

(22) Filed: Sep. 19, 2016

(65) Prior Publication Data
US 2018/0078789 A1  Mar. 22, 2018

(51) Int. Cl.
*A61N 5/10* (2006.01)

(52) U.S. Cl.
CPC ......... *A61N 5/1042* (2013.01); *A61N 5/1031* (2013.01); *A61N 5/1039* (2013.01); *A61N 5/1045* (2013.01); *A61N 5/1047* (2013.01)

(58) Field of Classification Search
CPC .. A61N 5/1042; A61N 5/1045; A61N 5/1031; A61N 5/1039; A61N 5/1047
See application file for complete search history.

(56) References Cited

U.S. PATENT DOCUMENTS
2008/0242969 A1  10/2008  Sayeh et al.

FOREIGN PATENT DOCUMENTS
| CN | 103706044 | 4/2014 |
| EP | 2266664 | 12/2010 |

OTHER PUBLICATIONS

Gevaert et al. "Implementation of HybridArc treatment technique in preoperative radiotherapy of rectal cancer: dose patterns in target lesions and organs at risk as compared to helical Tomotherapy and RapidArc" Radiation Oncology, 7:120 (Year: 2012).*
Matuszak et al. "FusionArc optimization: A hybrid VMAT/IMRT planning strategy" Med. Phys. 40(7) (Year: 2013).*
International Application No. PCT/EP2017/073422, "International Search Report and Written Opinion", dated Jan. 4, 2018, 12 pages.

* cited by examiner

*Primary Examiner* — Kaylee R Wilson
(74) *Attorney, Agent, or Firm* — Kilpatrick Townsend & Stockton LLP

(57) ABSTRACT

In a radiation treatment plan that includes a plurality of treatment fields of multiple treatment modalities, such as IMRT modality and dynamic treatment path modality (e.g., VMAT and conformal arc therapy), an optimized spatial point sequence may be determined that optimizes the total treatment time, which includes both the beam-on time (i.e., during the delivery of radiation dose) and the beam-off time (i.e., during transitions between consecutive treatment fields). The result is a time-ordered field trajectory that intermixes and interleaves different treatment fields. In one embodiment, a dynamic treatment path may be cut into a plurality of sections, and one or more IMRT fields may be inserted between the plurality of sections.

23 Claims, 16 Drawing Sheets

GENERATING TIME-EFFICIENT TREATMENT FIELD TRAJECTORIES FOR EXTERNAL-BEAM RADIATION TREATMENTS

CROSS-REFERENCES TO RELATED APPLICATIONS

The following two U.S. Patent Applications (including this one) are being filed concurrently, and the entire disclosure of the other application is incorporated by reference into this application for all purposes:

U.S. application Ser. No. 15/269,870, filed Sep. 19, 2016, entitled "GENERATING TIME-EFFICIENT TREATMENT FIELD TRAJECTORIES FOR EXTERNAL-BEAM RADIATION TREATMENTS", and U.S. application Ser. No. 15/269,882, filed Sep. 19, 2016, entitled "OPTIMIZATION OF RADIATION TREATMENT PLANS FOR OPTIMAL TREATMENT TIME IN EXTERNAL-BEAM RADIATION TREATMENTS".

FIELD

The present disclosure relates generally to treatment planning for radiation therapy and is more particularly directed to generating a treatment field trajectory for a radiation treatment plan.

BACKGROUND

In general, radiation therapy consists of the use of ionizing radiation to treat living tissue, usually tumors. There are many different types of ionizing radiation used in radiation therapy, including high energy x-rays, electron beams, and proton beams. The process of administering the radiation to a patient can be somewhat generalized regardless of the type of radiation used.

Modern radiation therapy techniques include the use of Intensity Modulated Radiotherapy ("IMRT"), typically by means of an external radiation treatment system, such as a linear accelerator, equipped with a multileaf collimator ("MLC"). Use of multileaf collimators in general, and an IMRT field in particular, allows the radiologist to treat a patient from a given direction of incidence to the target while varying the shape and dose of the radiation beam, thereby providing greatly enhanced ability to deliver radiation to a target within a treatment volume while avoiding excess irradiation of nearby healthy tissue. However, the greater freedom which IMRT and other complex radiotherapy techniques, such as volumetric modulated arc therapy (VMAT, where the system gantry moves while radiation is delivered) and three-dimensional conformal radiotherapy ("3D conformal" or "3DCRT"), afford to radiologists has made the task of developing treatment plans more difficult. As used herein, the term radiotherapy should be broadly construed and is intended to include various techniques used to irradiate a patient, including use of photons (such as high energy x-rays and gamma rays), particles (such as electron and proton beams), and radiosurgical techniques. While modern linear accelerators use MLCs, other methods of providing conformal radiation to a target volume are known and are within the scope of the present invention.

Several techniques have been developed to create radiation treatment plans for IMRT or conformal radiation therapy. Generally, these techniques are directed to solving the "inverse" problem of determining the optimal combination of angles, radiation doses and MLC leaf movements to deliver the desired total radiation dose to the target, or possibly multiple targets, while minimizing irradiation of healthy tissue. This inverse problem is even more complex for developing arc therapy plans where the gantry is in motion while irradiating the target volume. Heretofore, radiation oncologists or other medical professionals, such as medical physicists and dosimetrists, have used one of the available algorithms to develop and optimize a radiation treatment plan.

A radiation treatment plan may include treatment fields of multiple treatment modalities, such as IMRT, VMAT, and 3DCRT. The administration of a complex series of fields can be a slow process. Transitions between consecutive treatment fields may involve long travel distances for the treatment axes of the radiation treatment system. A radiation treatment system typically has certain maximum speed limits for the treatment axes. Therefore, longer travel distances for the treatment axes generally lead to longer transition times, and consequently longer total treatment times. Furthermore, the administration of a complex series of treatment fields may require human supervision and manual adjustment of the patient support when transitioning between treatment fields due to small patient-to-machine and machine-to-machine clearance margins.

Therefore, it is desirable to develop a treatment field trajectory that requires a relatively short total treatment time. It is also desirable to optimize radiation treatment plans for optimal treatment time.

BRIEF SUMMARY

According to embodiments of the present invention, in a radiation treatment plan that includes a plurality of treatment fields of multiple treatment modalities, such as IMRT modality and dynamic treatment path modality (e.g., VMAT and conformal arc therapy), an optimized spatial point sequence is determined that optimizes the total treatment time, which includes both the beam-on time (i.e., during the delivery of radiation dose) and the beam-off time (i.e., during transitions between consecutive treatment fields). The result is a patient-specific and collision-free field trajectory that intermixes and interleaves different treatment fields, with non-radiative transitions between consecutive treatment fields. In one embodiment, a dynamic treatment path may be cut into a plurality of sections, and one or more IMRT fields may be inserted between the plurality of sections.

In another aspect of the present invention, an optimized radiation treatment plan is developed in which the total monitor unit (MU) count is taken into account. According to an embodiment, a planner may specify a maximum treatment time. An optimization algorithm converts the specified maximum treatment time to a maximum total MU count, which is then used as a constraint in the optimization process. According to an embodiment, a cost function for the optimization algorithm includes a term that penalizes any violation of the upper constraint for the MU count.

Other embodiments are directed to systems and computer readable media associated with methods described herein.

A better understanding of the nature and advantages of embodiments of the present invention may be gained with reference to the following detailed description and the accompanying drawings.

DEFINITIONS

Figure 1:
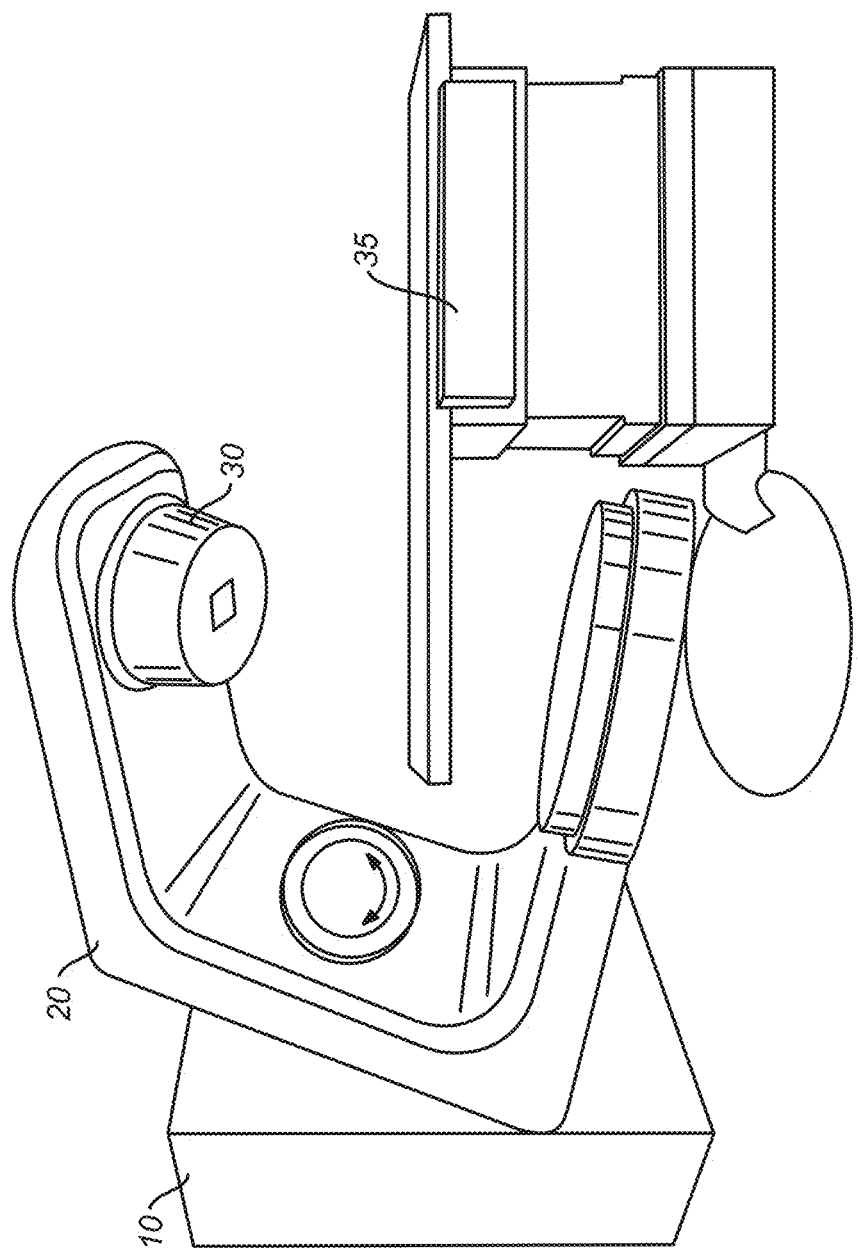
FIG. 1 is a schematic perspective view of a radiation treatment system.

"Radiation" refers to any particles (e.g., photons, electrons, protons etc.) used to treat tissue, e.g., tumors. Examples of radiation include high energy x-rays, gamma rays, electron beams, and proton beams. The different particles can correspond to different types of radiation treatments. The "treatment volume" refers to the entire volume that will be subjected to radiation, and is sometimes referred to as the "irradiated volume." The "target structure", "target volume", and "planning target volume" ("PTV") refer to tissue intended to receive a therapeutic prescribed dose.

A "radiation treatment plan" can include a dose distribution, machine parameters for achieving the dose distribution for a given patient, and information about the given patient. A dose distribution provides information about the variation in the dose of radiation with position. A "dose distribution" can take many forms, e.g., a dose volume histogram (DVH) or a dose matrix. A DVH can summarize three-dimensional (3D) dose distributions in a graphical 2D format, e.g., where the horizontal axis is the dose (e.g., in units of grays—Gy) absorbed by the target structure (e.g., a tumor) and the vertical axis is the volume percentage. In a differential DVH, the height of a bar at a particular dose indicates the volume of the target structure receiving the particular dose. In a cumulative DVH, the height of a bar at a particular dose represents the volume of the structure receiving greater than or equal to that dose. The cumulative DVH is generally a curve (e.g., when small bin sizes are used), whereas the differential DVH is generally a disjoint bar graph. A drawback of a DVH is that it offers no spatial information; i.e., a DVH does not show where within a structure a dose is received. A dose matrix can provide the dose that each part of the body receives.

A "dose prediction model" receives patient data and outputs a dose distribution that is predicted to be obtainable. A model can also output other data, such as optimization objectives. Different types of radiation treatments can have different models. The patient data can include diagnostic information (e.g., general tumor location or stage information) and geometric information (e.g., the spatial geometry of the tumor and of other organs in the patient). A particular model can have an accuracy (reliability) associated with the predicted dose distribution. The accuracy can be determined from a set of test radiation treatment plans whose dose distribution has been determined via other means (e.g., by optimizing a cost function). For example, the accuracy can be determined based on how well the model predicts the actual dose distributions obtained by optimizing a cost function.

"Monitor unit" (MU) is a measure of machine output from a clinical accelerator for radiation therapy such as a linear accelerator. Monitor units are measured by monitor chambers, which are ionization chambers that measure the dose delivered by a beam and built into the treatment head of radiotherapy linear accelerators. Linear accelerators are calibrated to give a particular absorbed dose under particular conditions, although the definition and measurement configuration will vary between centers.

Two common definitions of monitor units are: (1) the monitor chamber reads 100 MU when an absorbed dose of 1 gray (100 rads) is delivered to a point at the depth of maximum dose in a water-equivalent phantom whose surface is at the isocenter of the machine (i.e. usually at 100 cm from the source) with a field size at the surface of 10 cm×10 cm; and (2) the monitor chamber reads 100 MU when an absorbed dose of 1 Gy (100 rad) is delivered to a point at a given depth in the phantom with the surface of the phantom positioned so that the specified point is at the isocenter of the machine and the field size is 10 cm×10 cm at the isocenter.

Some linear accelerators are calibrated using source-to-axis distance (SAD) instead of source-to-surface distance (SSD), and calibration (monitor unit definition) may vary depending on hospital custom. Early radiotherapy was performed using "constant SSD" treatments, and so the definition of monitor unit was adopted to reflect this calibration geometry. Modern radiotherapy is performed using isocentric radiation treatment plans, so newer definitions of the monitor unit are based on geometry at the isocenter based on the source-to-axis distance (SAD).

The term "spatial point" used in this disclosure in relation to a treatment field refers to a geometrical point associated with a set of values for treatment axes coordinates of an external-beam radiation treatment system. A spatial point is defined by the position of the isocenter, the position and angles of the patient support, the gantry angle, the collimator angle, and the position of each MLC leaf. The term "control point" refers to a parametrical point of a radiation treatment field that includes spatial information about the treatment axes as well as the MU count and/or the related concept of the meterset weight.

DETAILED DESCRIPTION

In one aspect of the present invention, in a radiation treatment plan that includes a plurality of treatment fields of multiple treatment modalities, such as IMRT modality and dynamic treatment path modality (e.g., VMAT and conformal arc therapy), an optimized spatial point sequence may be determined that optimizes the total treatment time, which includes both the beam-on time (i.e., during the delivery of radiation dose) and the beam-off time (i.e., during transitions between consecutive treatment fields). The spatial points that define directions of incidence of radiation in the plurality of treatment fields are received as input. An optimization algorithm reorders the chronological order of the spatial points to achieve an optimized treatment field trajectory that optimizes the total treatment time. The spatial points during beam-on are not modified by the optimization process. Any new spatial points introduced are ones at which no dose is delivered. In some embodiments, the optimized treatment field trajectory may intermix and interleave the plurality of treatment fields of multiple treatment modalities. In one embodiment, a dynamic treatment path may be cut into a plurality of sections, and one or more IMRT fields may be inserted between the plurality of sections.

According to embodiments of the invention, the optimization algorithm takes into account the dynamics of the treatment axes of the radiation treatment system, such as isocenter location, gantry angle, couch angles (rotation, pitch, and yaw), and couch offsets (X, Y, and Z coordinates), and the positions of other components associated with the patient support during beam-on. According to some embodiments, the optimization algorithm further takes into account clinical protocols and system hardware constraints in achieving a time-efficient treatment field trajectory. Clinical protocols may include the treatment axes coordinates at which the patient can be loaded onto the couch (i.e., the initial clinical condition), the treatment axes coordinates at which the patient can be unloaded off the couch (i.e., the end clinical condition), and the treatment axes coordinates at which the patient is to be imaged. Other system hardware constraints may include patient-to-machine clearance limits, machine-to-machine clearance limits, and other predefined plan quality defined by metrics other than those defining dosimetric plan quality. The result is a spatial-point sequence that is collision-free and requires minimal human intervention during delivery, as well as achieving optimal total treatment time.

In another aspect of the present invention, an optimized radiation treatment plan is developed in which the total monitor unit (MU) count is taken into account. According to an embodiment, a planner may specify a maximum treatment time. An optimization algorithm converts the specified maximum treatment time to a maximum total MU count, which is then used as a constraint in the optimization process.

The conversion from the specified maximum treatment time to a maximum total MU count depends on a number of factors, which may include: the selected dose rate of the radiation machine, absolute calibration of the radiation machine, maximum speed limits of various treatment axes (including MLC leaf positions), and the selected treatment fields and the associated field geometries. Other factors, such as time for patient imaging and positioning, may also be considered. The field geometries affects the MU count, because more fields in general produces more modulation, which in turn requires more MUs. There are also more complex effects. For example, the "sliding window" technique of IMRT requires MLC leaf movement during delivery of the IMRT field, which causes more MUs since MLC leaf movement takes a finite time. If the number of fields is increased, the transition times between the fields may be increased, since the total travel distances of the treatment axes are increased.

According to an embodiment, a cost function for the optimization algorithm includes a term that penalizes any violation of the upper constraint for the MU count. For example, the cost function may include a term that is proportional to the square of the total MU count of a radiation treatment plan in excess of the maximum total MU count. In other embodiments, the cost function term may be of other functions of the total MU count of a radiation treatment plan in excess of the maximum total MU count. For example, it could be a polynomial function of an order greater than two, or it could be an exponential function. According to some embodiments, to lower the MU count, the algorithm may require more fluence smoothing by assigning a stronger smoothing constraint.

I. Treatment System

External beam therapy (EBT), also called external radiation therapy, is a method for delivering a beam or several beams of high-energy x-rays to a patient's tumor. Beams are generated outside the patient (usually by a linear accelerator) and are targeted at the tumor site.

Figure 2:
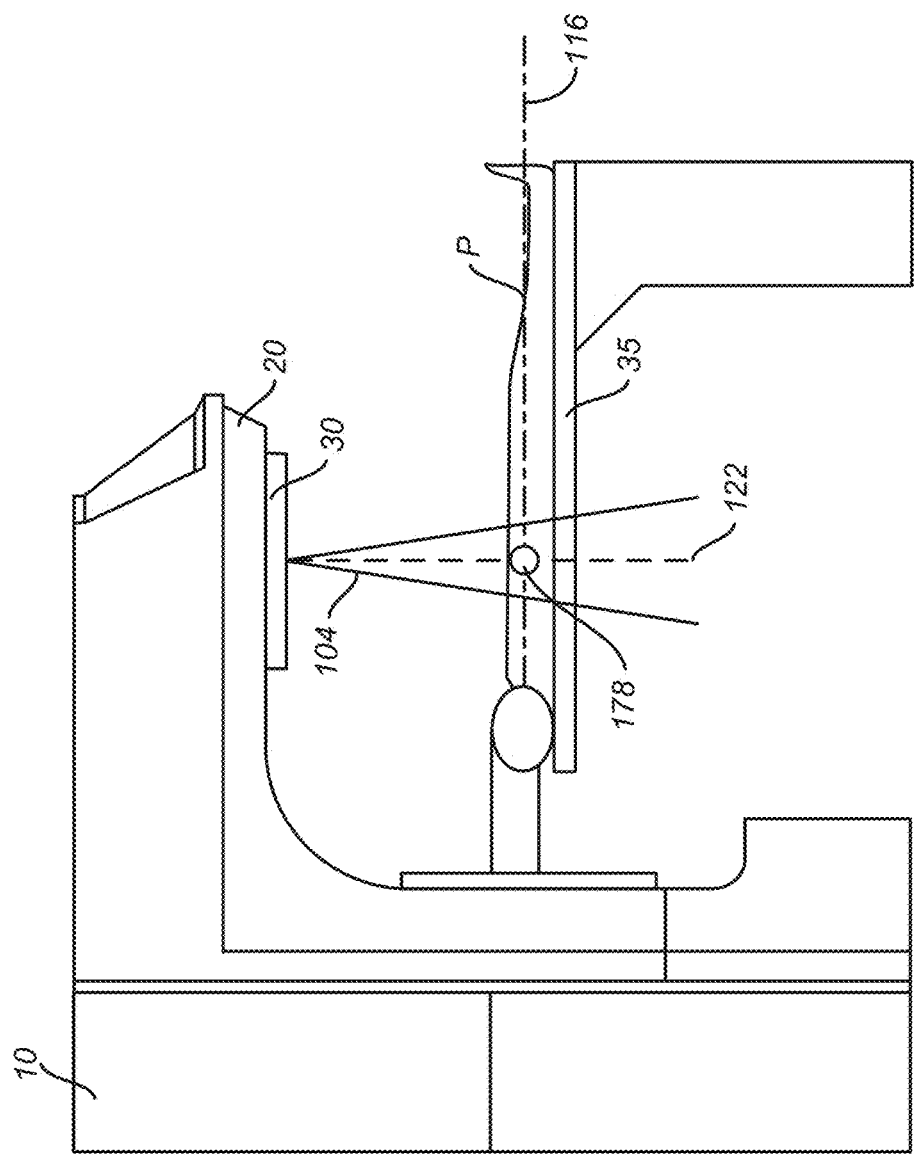
FIG. 2 is a schematic side view of a radiation treatment system.

FIGS. 1 and 2 depict a radiation treatment system of the type which may be used in connection with the present invention. Referring to FIG. 1, a perspective view of radiation treatment system (in this case a linear accelerator) is shown. Typically, such a system is capable of generating either an electron (particle) beam or an x-ray (photon) beam for use in the radiotherapy treatment of patients on a treatment couch 35. Other radiation treatment systems are capable of generating heavy ion particles such as protons. For purposes of the present discussion, only x-ray irradiation will be discussed. However, it will be appreciated by those skilled in the art that the same principles apply to other systems.

Stand 10 supports a rotatable gantry 20 with a treatment head 30. Next to stand 10 there is arranged a control unit (not shown) which includes control circuitry for controlling the different modes of operation of the accelerator. A high voltage source is provided within the stand or in the gantry, to supply voltage to an electron gun (not shown) positioned on an accelerator guide located in the gantry 20. Electrons are emitted from the electron gun into the guide (not shown) where they are accelerated. A source supplies RF (microwave) power for the generation of an electric field within the waveguide. The electrons emitted from the electron gun are accelerated in the waveguide by the electric field, and exit the waveguide as a high energy electron beam, typically at megavoltage energies. The electron beam then strikes a suitable metal target, emitting high energy x-rays in the forward direction.

Referring now to FIG. 2, a somewhat more detailed side view of a radiation treatment system of the type which may be used in connection with the present invention is shown. A patient P is shown lying on the treatment couch 35. X-rays formed as described above are emitted from the target in the treatment head 30 in a divergent beam 104. Typically, a patient plane 116, which is perpendicular to the page in FIG. 2, is positioned about one meter from the x-ray source or target, and the axis of the gantry 20 is located on the plane 116, such that the distance between the target and the isocenter 178 remains constant when the gantry 20 is rotated. The isocenter 178 is at the intersection between the patient plane 116 and the central axis of beam 122. A treatment volume to be irradiated is located about the isocenter 178.

Figure 3:
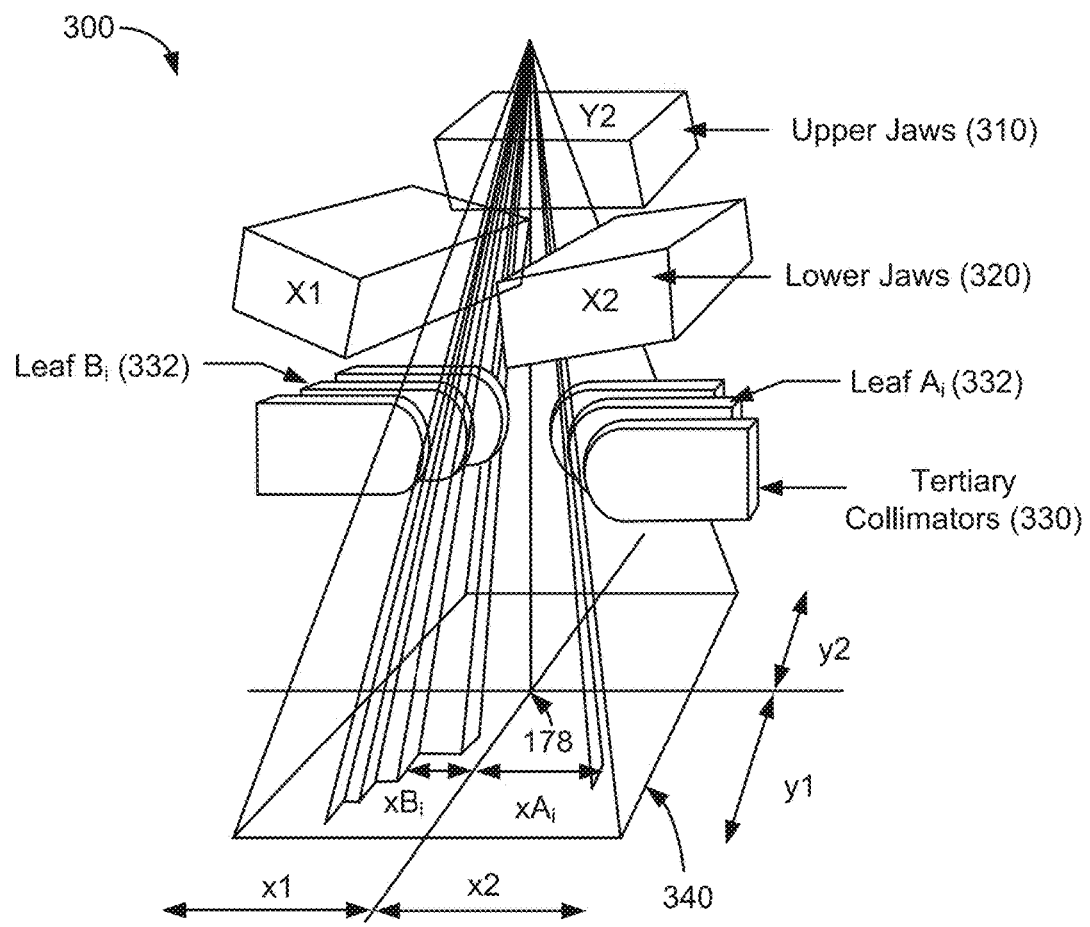
FIG. 3 shows schematically a photon collimation system in a radiation treatment system.

FIG. 3 shows schematically a photon collimation system 300 with upper jaws 310 (i.e., the Y1 and Y2 jaws; the Y1 jaw is omitted for clarity), lower jaws 320 (i.e., the X1 and X2 jaws), and a multileaf collimator (MLC) 330. The field dimensions in the plane 340 at the isocenter 178 are indicated. The upper jaws 310, the lower jaws 320, and the leaves 332 of the MLC 330 comprise an x-ray blocking material, and are positioned in the head 30 to define the width of the x-ray beam at the patient plane. Typically, the jaws 310 and 320 are moveable and, when fully open, define a maximum beam of about 40 cm×40 cm at the patient plane 116. The MLC 330 is positioned at the exit of the head 30, to further shape the x-ray beam. Since its introduction in 1990 the MLC has become a standard feature of most radiation treatment systems. Current MLCs sold by the assignee of the present invention use up to 120 individually controllable leaves, typically thin slices of tungsten, that can be moved into or out of the x-ray beam under the control of system software.

Figure 4:
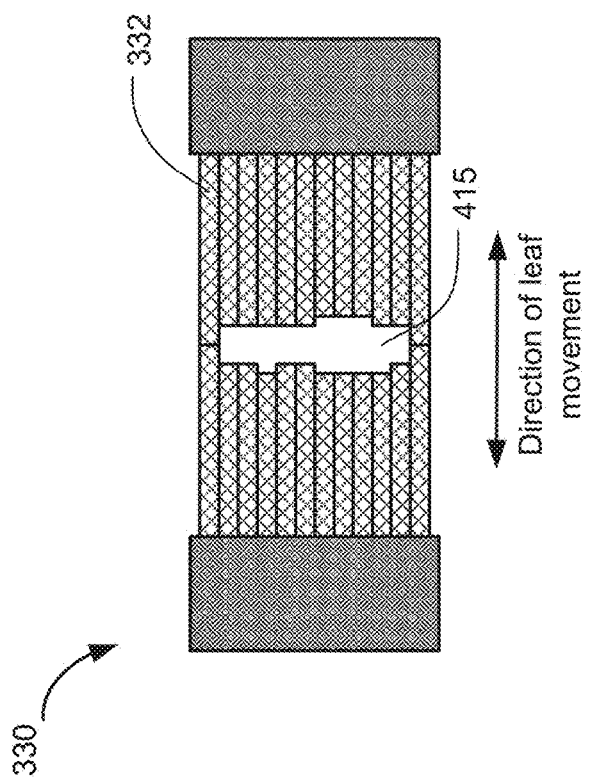
FIG. 4 shows an exemplary multileaf collimator (MLC) plane.

FIG. 4 shows an exemplary MLC plane having a plurality of leaves 332, arranged in opposing pairs, and an aperture 415 created by selected leaf movements. Radiation passes through and is shaped by the aperture 415. Thus, the MLC can be used to collimate the x-rays to provide conformal treatment of tumors from various angles ("3D conformal,") as well as intensity modulated radiotherapy ("IMRT"), whereby different radiation doses are delivered to different portions of the treatment area. The treatment volume, i.e., the irradiated volume proximate to the isocenter 178 in the treatment path of the x-ray beam, is defined by the jaws 310 and 320, the leaf sequence of the MLC 330, and the collimator angle, i.e., the angle at which the MLC 330 sits in the head 30.

Figure 5:
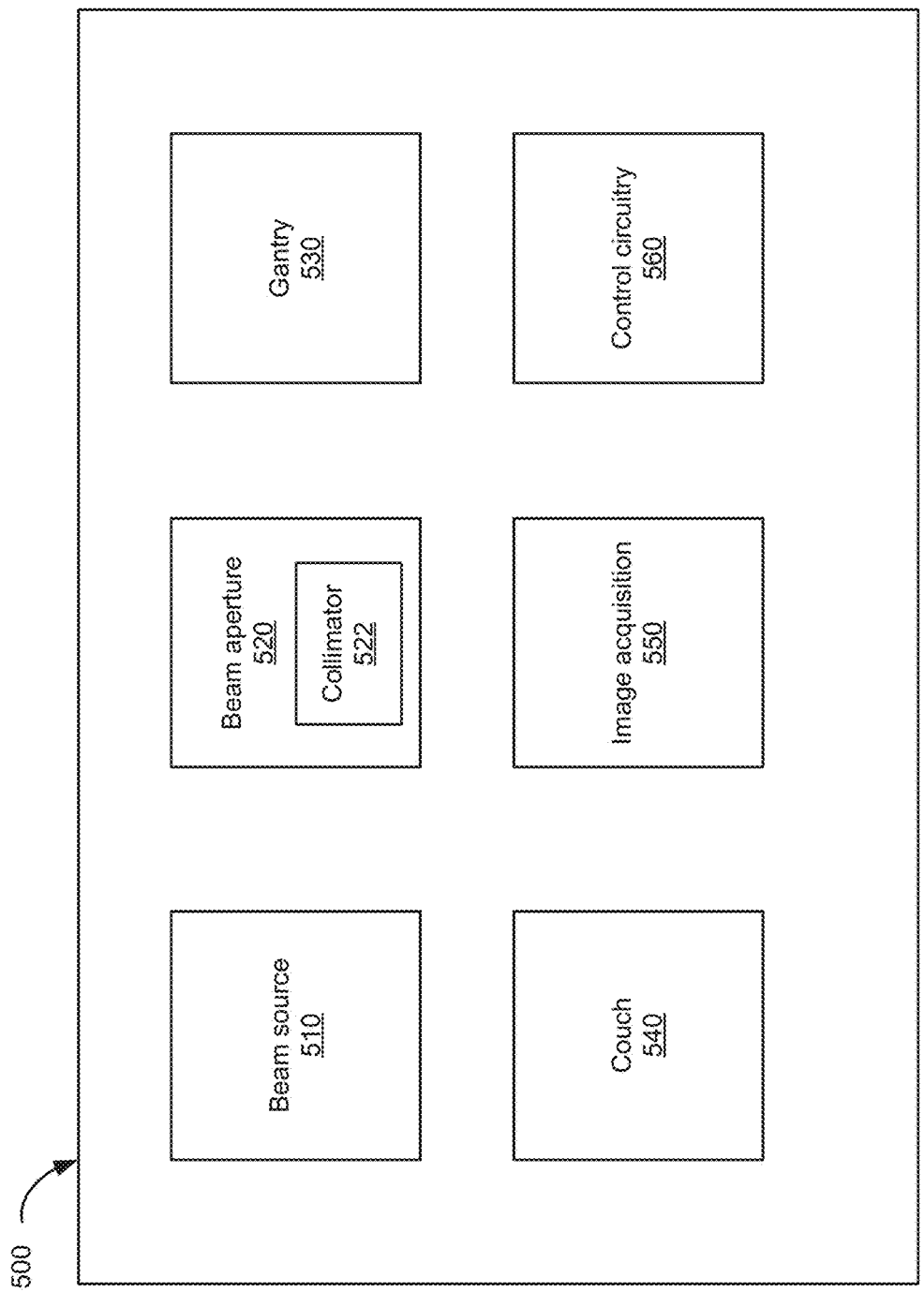
FIG. 5 shows a block diagram of an external-beam radiation treatment system of FIGS. 1 and 2.

FIG. 5 shows a block diagram of an external-beam radiation treatment system 500 of FIGS. 1 and 2. The radiation treatment system 500 includes a beam source 510, a beam aperture 520, a gantry 530, and a couch 540. The beam source 510 is configured to generate a beam of therapeutic radiation. This beam of radiation may include x-rays, particles, and the like. The beam aperture 520 includes an adjustable multi-leave collimator (MLC) 522 for spatially filtering the radiation beam. The couch 540 is configured to support and position a patient. The couch 540 may have six degrees of freedom, namely the translational offsets X, Y, and Z, and the rotation, pitch, and yaw.

The gantry 530 that circles about the couch 540 houses the beam source 510 and the beam aperture 520. The beam source 510 is optionally configured to generate imaging radiation as well as therapeutic radiation. The radiation treatment system 500 may further include an image acquisition system 550 that comprises one or more imaging detectors mounted to the gantry 530.

The radiation treatment system 500 further includes a control circuitry 560 for controlling the operation of the beam source 510, the beam aperture 520, the gantry 530, the couch 540, and the image acquisition system 550. The control circuitry 560 may include hardware, software, and memory for controlling the operation of these various components of the radiation treatment system 500. The control circuitry 560 can comprise a fixed-purpose hard-wired platform or can comprise a partially or wholly-programmable platform. The control circuitry 560 is configured to carry out one or more steps, actions, and other functions described herein. In some embodiments, the control circuitry 560 may include a memory for receiving and storing a radiation treatment plan that defines the spatial points of one or more treatment fields. The control circuitry 560 may then send control signals to the various components of the radiation treatment system 500, such as the beam source 510, the beam aperture 520, the gantry 530, and the couch 540, to execute the radiation treatment plan. In some other embodiments, the control circuitry 560 may include an optimization engine to determine a radiation treatment plan.

II. Treatment Modalities and Treatment Planning

A radiation treatment plan may include one or more treatment modalities. For example, it may include an IMRT modality where the direction of incidence to a treatment target is fixed during beam-on, and a dynamic treatment path modality where the direction of incidence to a treatment target changes during continuous irradiation, as further described below.

A. Intensity Modulated Radiotherapy (IMRT)

In an IMRT modality, only the MLC leaves and collimator jaws move, while other treatment axes, such as the isocenter location, gantry angle, couch angles (including rotation, pitch, and yaw), and couch offsets, are fixed during beam on. IMRT allows control over the radiation doses delivered to specific portions of the site being treated. In particular, IMRT allows the intensity distribution of the radiation reaching the patient to have almost any arbitrary distribution. IMRT can be implemented by iteratively positioning the leaves 332 of the MLC 330, which form an aperture 415 through which radiation is delivered, to provide desired field shapes which collectively deliver the desired dose distribution.

Figure 6:
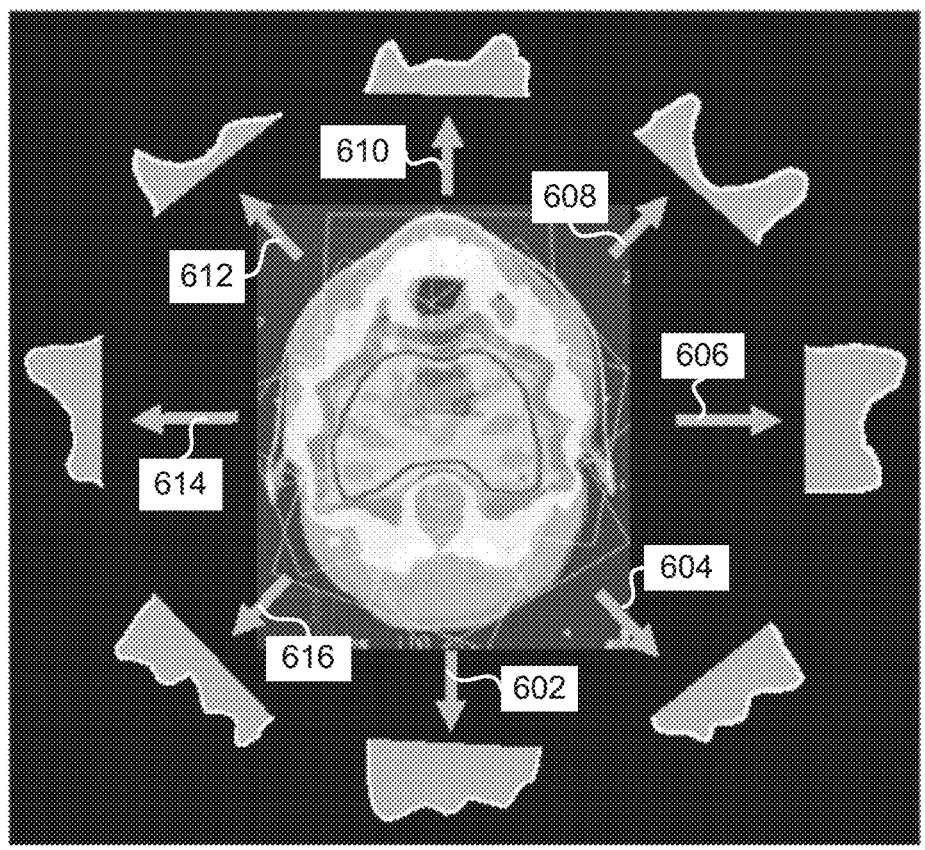
FIG. 6 illustrates schematically a conventional IMRT technique that involves administering IMRT fields at a finite number of well-chosen incidence angles.

FIG. 6 illustrates schematically a conventional IMRT technique, which involves administering IMRT fields at a finite number of well-chosen angles of incidence 602-616 (referred to as spatial points), where the radiation beam is off as the gantry is moved from one angle to the next.

IMRT techniques can either be static ("step and shoot"), in the sense that the leaves do not move when the beam is on (they are rearranged in steps between beam-on shots), or alternatively be dynamic using a "sliding window" approach, in which the leaves of the MLC are moved continuously when the beam is on. Specifically, in sliding-window IMRT the overall speed of leaf motion and the separation of leaf pairs are independently adjusted as the window moves, such that different portions of the treatment field are irradiated with different doses of radiation through an aperture that changes shape as it is being moved.

B. Dynamic Treatment Paths

Treatment paths, where the direction of incidence to the treatment target changes while radiation is administered, are referred to herein as "dynamic treatment path" modalities. Dynamic treatment paths enable plans of comparable quality to be delivered in less time. Dynamic treatment paths include, for example, intensity modulated arc therapy (IMAT), volumetric modulated arc therapy (VMAT), and conformal arc therapy. A VMAT treatment involves one or multiple appropriately optimized intensity-modulated arcs in which radiation is administered with simultaneous gantry rotation and MLC motion. The terminals of the arc are defined by two spatial points. VMAT differs from conventional IMAT in that it delivers dose to the whole volume, rather than slice by slice. A VMAT arc can be either coplanar or non-coplanar. A coplanar VMAT arc refers to the case where the couch rotation angle is fixed at zero degree as the gantry rotates during beam-on. A non-coplanar VMAT arc refers to the case where the couch rotation angle is fixed at a non-zero degree angle as the gantry rotates during beam-on, i.e., the couch is not parallel to the axis of rotation of the gantry. Dynamic treatment paths can also include coronal arc, where the gantry is fixed and the couch rotates during continuous irradiation.

In this disclosure, the term "dynamic treatment path" does not include the so-called burst-mode rotational IMRT (rIMRT) or the Siemens mARC (stands for "modulated arc"). In rIMRT or mARC, the beam is turned off during MLC motion between arclets (i.e., sectors of an arc); when the MLC leaves are fixed, the beam is turned on while the gantry rotates along an arclet, delivering "step-and-shoot" IMRT in a rotational manner.

C. Radiation Treatment Planning

Radiation therapy is generally implemented in accordance with a radiation treatment plan which typically takes into account the desired dose of radiation that is prescribed to be delivered to the tumor, as well as the maximum dose of radiation which can be delivered to surrounding tissue. Various techniques for developing radiation treatment plans may be used. Preferably, the computer system used to develop the radiation treatment plan provides an output that can be used to control the radiation treatment system, including the spatial points and the MLC leaf movements. Typically, the desired dose prescribed in a radiation treatment plan is delivered over several sessions, called fractions.

Several techniques have been developed to create radiation treatment plans for IMRT or conformal radiation therapy. Generally, these techniques are directed to solving the "inverse" problem of determining the optimal combination of angles, radiation doses and MLC leaf movements to deliver the desired total radiation dose to the target while minimizing irradiation of healthy tissue. This inverse problem is even more complex for developing arc therapy plans where the gantry is in motion while irradiating the target volume. Heretofore, radiation oncologists or other medical professionals, such as medical physicists and dosimetrists, have used one of the available algorithms to develop and optimize a radiation treatment plan.

Typically, such planning starts with volumetric information about the target tumor and about any nearby tissue structures. For example, such information may comprise a map of the planning target volume ("PTV"), such as a prostate tumor, which is prescribed by the physician to receive a certain therapeutic radiation dose with allowable tolerances. Volumetric information about nearby tissues may include for example, maps of the patient's bladder, spinal cord and rectum, each of which may be deemed an organ at risk (OAR) that can only receive a much lower, maximum prescribed amount of radiation without risk of damage. This volumetric information along with the prescribed dose limits and similar objectives set by the medical professionals is the basis for calculating an optimized dose distribution, also referred to as fluence map, which in turn is the basis for determining a radiation treatment plan. The volumetric information may, for example, be reduced to an objective function or a single figure of merit that accounts for the relative importance of various trade-offs inherent in a radiation treatment plan, along with constraints that must be met for the radiation treatment plan to be medically acceptable or physically possible.

Treatment planning algorithms can account for the capabilities of the specific radiation treatment system they are used with. For example, the type, energy level and fluence of the radiation beam, and the capabilities of the MLC. Generally speaking, treatment planning algorithms proceed by calculating the radiation dose received by each voxel in the treatment volume, adjusting one or more variable system parameters, such as the angle of irradiation or the positions of the MLC leaves, and then recalculating the dose received by each voxel. This process is ideally performed iteratively until an optimized plan is reached. However, the amount of time needed to perform the large number of calculations for each iteration places a practical limit on the number of iterations that can be performed. Accordingly, the algorithm is terminated after a predetermined amount of time, after a predetermined number of iterations, or after some other practical limit is reached. Generally speaking, there is a trade-off between the accuracy and speed of the different algorithms available for treatment planning.

III. Generating Time-Efficient Treatment Field Trajectories

It is desirable to develop a treatment field trajectory that delivers the prescribed dose in a relatively short total treatment time. Besides affording more patient comfort, a shorter treatment time may reduce the chance of over exposure to nearby organs at risk, since the surrounding organs may change positions during the course of a treatment. The total treatment time for a radiation treatment plan may include beam-on time and beam-off time. Beam-on time is the total duration of time while radiation dose is being delivered, and may depend on factors such as the prescribed dose, the planned treatment volume, the selected dose rate of the radiation machine, the maximum speeds of the treatment axes, and the treatment field geometries. The beam-off time includes transition times between consecutive treatment fields. Transition times between consecutive treatment fields include times required for the treatment axes, such as the isocenter location, gantry angle, couch angles (including rotation, pitch, and yaw), and couch offsets, to move from an end spatial point of one treatment field to a start spatial point of the next treatment field. Transition times may depend on factors such as the travel distances of the treatment axes between consecutive treatment fields, and the maximum speeds of the treatment axes of the radiation treatment system.

An external-beam radiation treatment plan may include a plurality of treatment fields of multiple treatment modalities, such as IMRT (either static or dynamic IMRT) modality and dynamic treatment path modality (e.g., VMAT and conformal arc therapy). The administration of a complex series of fields can be a slow process. Transitions between consecutive treatment fields may involve long travel distances for the treatment axes of the radiation treatment system. A radiation treatment system typically has certain maximum speed limits for the treatment axes. For example, the gantry speed may be limited to about 6°/s or other values. Therefore, longer travel distances for the treatment axes generally lead to longer transition times, and consequently longer total treatment times. Furthermore, the administration of a complex series of treatment fields may require human supervision and manual adjustment of the patient support when transitioning between treatment fields due to small patient-to-machine and machine-to-machine clearance margins.

Figure 7:
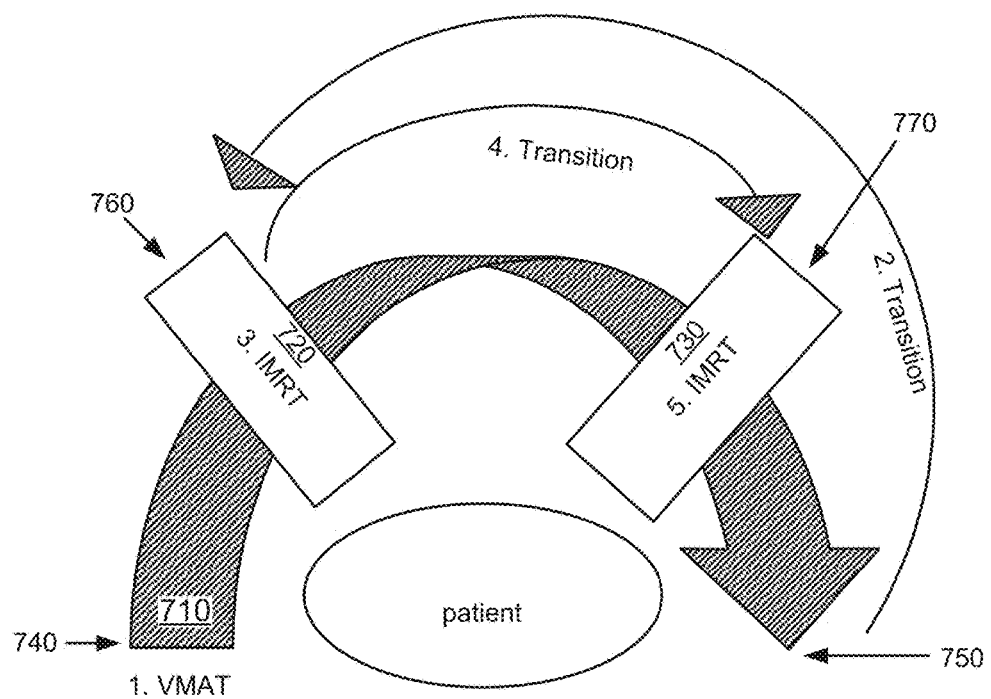
FIG. 7 illustrates schematically an example treatment field trajectory according to an embodiment.

FIG. 7 illustrates schematically an example treatment field trajectory of a radiation treatment plan. In this example, the radiation treatment plan includes one VMAT field 710 and two IMRT fields 720 and 730, to be administered according to the following chronological order: (1) the VMAT field 710 from a start spatial point 740 to an end spatial point 750; (2) the first IMRT field 720 at a first spatial point 760; and (3) the second IMRT field 730 at a second spatial point 770. At the end of the VMAT field 710, the treatment axes of the radiation treatment system would need to move from the end spatial point 750 to the first spatial point 760 for the administration of the first IMRT field 720.

After the first IMRT field is completed, the treatment axes of the radiation treatment system would need to move from the first spatial point 760 to the second spatial point 770 for the administration of the second IMRT field 730. Each transition may involve relatively long spatial travels of the treatment axes, and therefore may lead to relatively long beam-off time and thus longer total treatment time.

Therefore, it may be desirable to generate a time-efficient treatment field trajectory, i.e., a spatial-point sequence, that organizes a plurality of treatment fields of a radiation treatment plan in a chronological order, such that transitions between consecutive treatment fields involve minimal spatial travels of the treatment axes and thus require minimal transition times. It is also desirable that the time-efficient treatment field trajectory takes into account clinical deliverability (i.e., compliant with the start and end constraints for patient loading and off-loading), is free from machine-to-machine and machine-to-patient collisions, and requires minimal human intervention during delivery of the treatment plan.

A. Ordered Treatment Field Trajectory

Generally, an initial radiation treatment plan may include N number of beam-on fields and N−1 number of beam-off transitions between consecutive beam-on fields. According to some embodiments, it is assumed that the spatial point(s) of each beam-on (i.e., dose-delivering) field are given and are optimized in terms of dosimetric plan quality. The N number of beam-on fields may involve multiple treatment modalities. For example, they may involve IMRT modality and dynamic treatment path modality (e.g., VMAT and conformal arc). According to embodiments of the present invention, the spatial points that define directions of incidence of radiation in the plurality of treatment fields are received as input. The optimization algorithm analyzes the treatment axes of beam-on movements, and modifies the chronological order of delivering the N number of beam-on fields such that the total treatment time is optimized. The spatial points during beam-on are not modified in the optimization process. Any new spatial points introduced are ones at which no dose is delivered. Modifying the order does not have any effect on the dosimetric quality of the radiation treatment plan.

According to some embodiments, the optimization algorithm further takes into account clinical protocols and system hardware constraints in achieving a time-efficient and collision-free treatment field trajectory. Clinical protocols may include the treatment axes coordinates at which the patient can be loaded onto the couch (i.e., the initial clinical condition), the treatment axes coordinates at which the patient can be unloaded off the couch (i.e., the end clinical condition), and the treatment axes coordinates at which the patient is to be imaged. Other system hardware constraints may include patient-to-machine clearance limits, machine-to-machine clearance limits, and other predefined plan quality defined by metrics other than those defining dosimetric plan quality. The result is a spatial-point sequence that is collision-free and requires minimal human intervention during delivery, as well as requiring optimal total treatment time.

Figure 8:
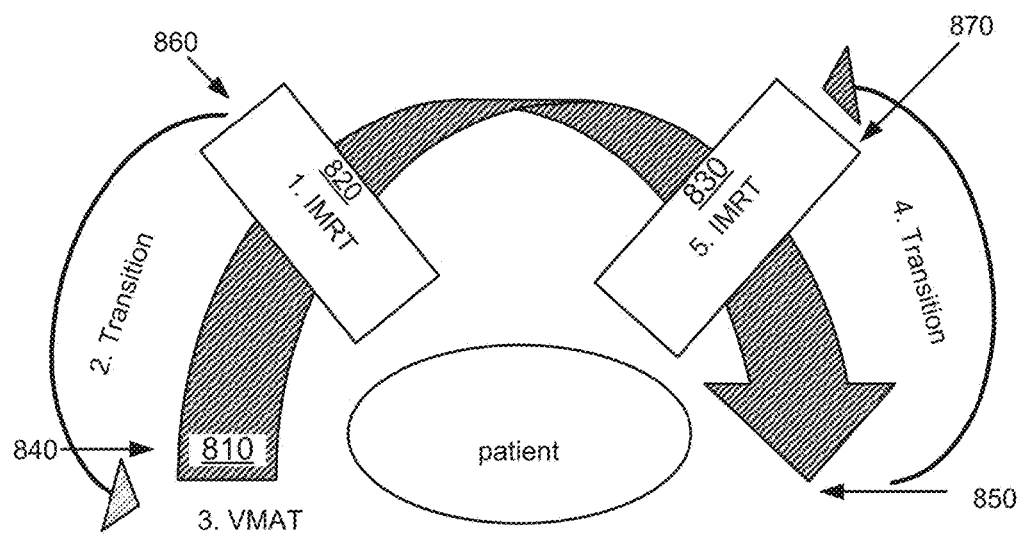
FIG. 8 illustrates schematically an example treatment field trajectory according to another embodiment.

FIG. 8 illustrates schematically an example optimized treatment field trajectory of a radiation treatment plan according to an embodiment. Similar to the radiation treatment plan illustrated in FIG. 7, this radiation treatment plan also includes one VMAT field 810 and two IMRT fields 820 and 830. Here, however, these treatment fields are administered in the following chronological order: (1) the first IMRT field 820 at a first spatial point 860; (2) the VMAT field 810 from a start spatial point 840 to an end spatial point 850; and (3) the second IMRT field 830 at a second spatial point 870.

After the first IMRT field 820 is completed, the treatment axes of the radiation treatment system are moved from the first spatial point 860 to the start spatial point 840 for the administration of the VMAT field 810. At the end of the VMAT field 810, the treatment axes of the radiation treatment system are moved from the end spatial point 850 to the second spatial point 870 for the administration of the second IMRT field 830. In this example, the distances the treatment axes of the radiation treatment system need to travel for the transition from the first spatial point 860 to the start spatial point 840 and for the transition from the end spatial point 850 to the second spatial point 870 may be relatively shorter as compared to the treatment field trajectory illustrated in FIG. 7.

Figure 9:
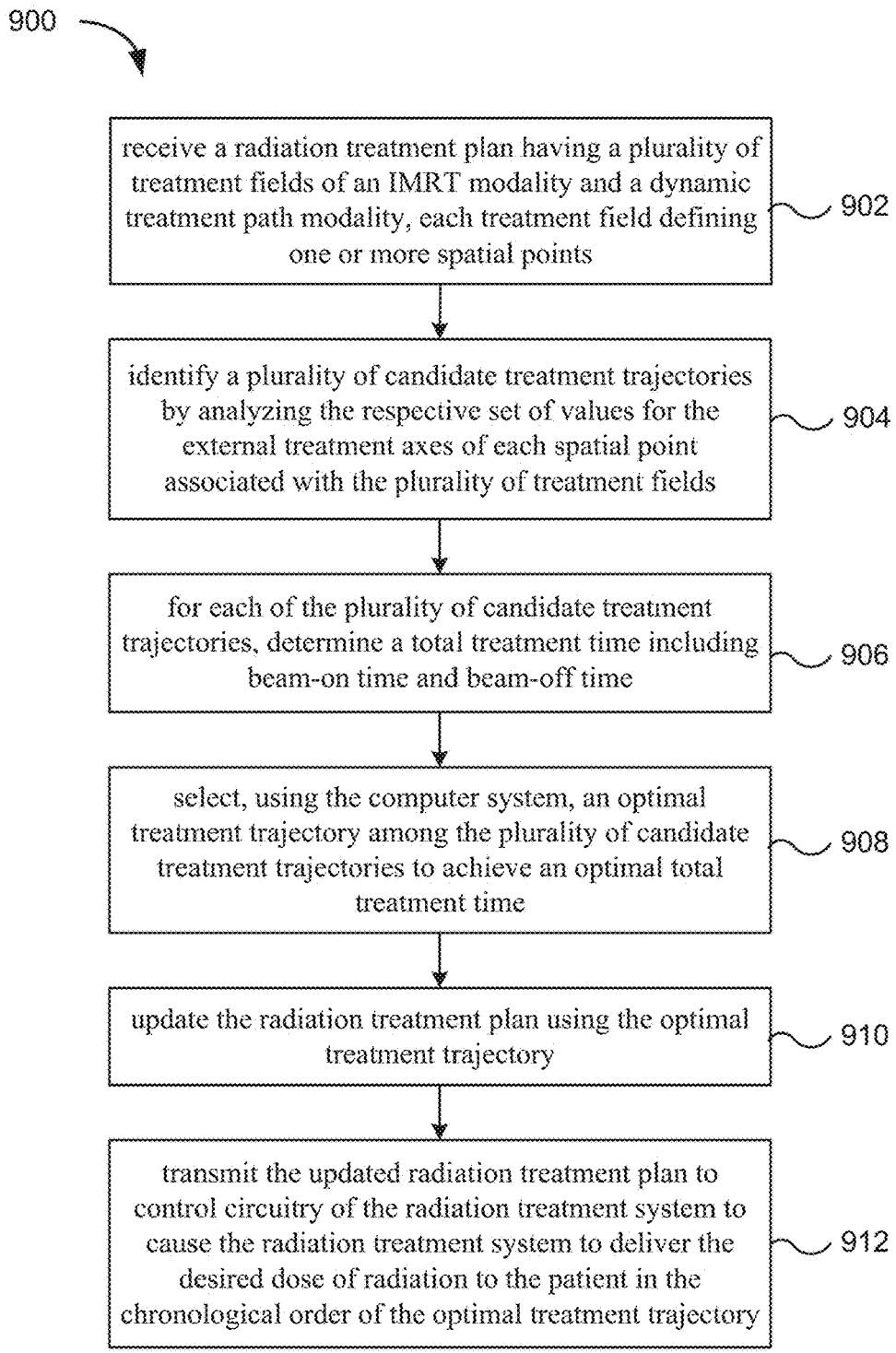
FIG. 9 is a simplified flowchart of a method of determining a treatment field trajectory according to an embodiment of the present invention.

FIG. 9 is a simplified flowchart of a method 900 of determining a treatment field trajectory for delivering a desired dose of radiation to a treatment volume within a patient using an external-beam radiation treatment system according to embodiments of the present invention. Method 900 can be performed wholly or partially with a computer system, as can other method described herein.

At 902, a radiation treatment plan is received. The radiation treatment plan includes a plurality of treatment fields of two or more different treatment modalities, such as a IMRT modality and a dynamic treatment path modality. Each treatment field defines one or more spatial points for delivering a respective portion of the desired dose. Each spatial point defines a set of values for treatment axes of the radiation treatment system, such as the isocenter location, gantry angle, couch angle, and couch offset. For example, assume that the radiation treatment plan includes N different beam-on treatment fields. There would be then (N−1) beam-off transitions in the treatment axes between the end of one field to the beginning of another field, if each treatment field is kept intact.

At 904, a plurality of candidate treatment trajectories are identified by analyzing the respective set of values for the treatment axes of each spatial point associated with the plurality of treatment fields. Each candidate treatment field trajectory comprises a chronological order of administering the plurality of treatment fields.

At 906, a total treatment time is determined for each of the plurality of candidate treatment trajectories. The total treatment time includes beam-on time when radiation dose is being delivered and beam-off time during transitioning of the treatment axes between consecutive treatment fields. Beam-on time is the total duration of time while radiation dose is being delivered. The beam-off time includes transition times between consecutive treatment fields.

At 908, an optimal treatment field trajectory is selected among the plurality of candidate treatment trajectories to achieve an optimal total treatment time. The optimization algorithm is analogous to the travelling salesman problem, where a salesman wants to visit a plurality of cities and would like to find the best way to do so such that it requires the minimal travel time. The optimal treatment field trajectory defines a spatial-point sequence that organizes the plurality of treatment fields in a chronological order, such that minimal transition time is achieved. The optimal treatment field trajectory is also collision-free and requires minimal human intervention during delivery of the treatment plan.

At 910, the radiation treatment plan is updated using the optimal treatment field trajectory. The updated radiation treatment plan specifies the chronological order of administering the plurality of treatment fields according to the optimal treatment field trajectory.

At 912, the updated radiation treatment plan is transmitted to control circuitry of the radiation treatment system to cause the radiation treatment system to deliver the desired dose of radiation to the patient in the chronological order of the optimal treatment field trajectory. The control circuitry sends control signals to various components of the radiation treatment system to sequentially set the treatment axes, such as the isocenter location, gantry angle, couch angles, couch offsets, MLC leaf sequence, and collimator angle, in accordance of the sequence of spatial points specified by the optimal treatment field trajectory.

According to some embodiments, the analysis of the treatment axes is carried out prior to the dosimetric optimization. In this case, the optimization algorithm may further determine the directional of traversal of a path of a treatment field of rotating-radiation-angle IMRT modality. For example, for a VMAT arc with two terminal spatial points A and B, the algorithm may determine whether the VMAT arc is to be traversed from A to B or from B to A. This is particularly relevant for fields that are of Varian's RapidArc type, since the treatment axes change throughout a RapidArc-type field.

According to some other embodiments, the analysis of the treatment axes is carried out after the dosimetric optimization. The optimization algorithm may assume that any treatment fields of dynamic treatment path modality are to be delivered in the directions determined by the dosimetric optimization. Alternatively, the optimization algorithm may also reverse the direction of a treatment field. If so, it may be necessary to change parameters that control and track the cumulative monitor unit (MU) count delivered by the treatment field. This may be the case for fields that are of Varian's RapidArc type that deliver dose from a number of incident directions.

In some other embodiments, the analysis of the treatment axes is carried out during dosimetric optimization. There might be multiple iterations between the two optimization processes.

B. Interleaving and Intermixing Treatment Modalities

According to some embodiments, in addition to reordering the sequence of administering a plurality treatment fields, the optimization algorithm may cut a given field into one or more sections to insert one or more of the other fields among the N number of beam-on fields at the cutlines, such that the total beam-off transition time is minimized. The result of the optimization is a patient-specific and time-ordered treatment field trajectory of spatial points that includes a combination of interleaved and intermixed modalities with non-radiative transitions therebetween.

Figure 10:
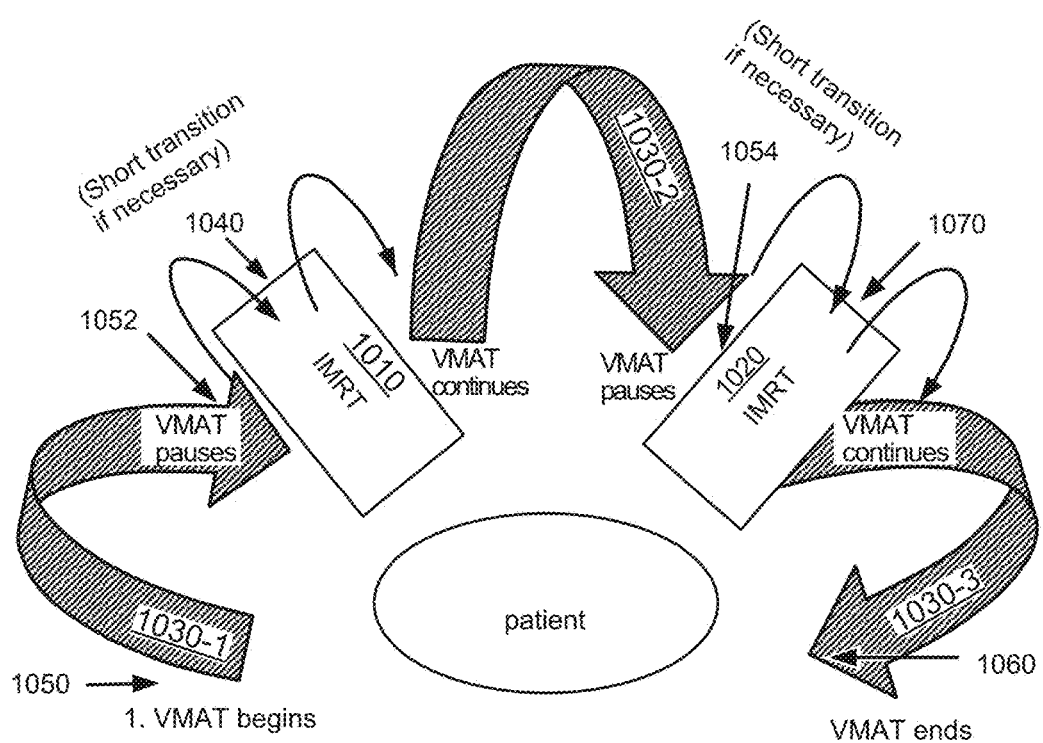
FIG. 10 illustrates schematically an example optimized treatment field trajectory involving interleaving a plurality of treatment fields according an embodiment of the present invention.

FIG. 10 illustrates schematically an example optimized treatment field trajectory of a radiation treatment plan according an embodiment of the present invention. In this example, similar to the treatment plans shown in FIGS. 7 and 8, this radiation treatment plan includes a first IMRT field 1010 at a first spatial point 1040, a second IMRT field 1020 at a second spatial point 1070, and a VMAT arc 1030 from a start spatial point 1050 to an end spatial point 1060. The first spatial point 1040 of the first IMRT field 1010 and the second spatial point 1070 of the second IMRT field 1020 may or may not lie on the same plane as that of the VMAT arc 1030.

Here, instead of delivering the entire VMAT arc 1030 at once, the VMAT arc 1030 is cut at two intermediate spatial points 1052 and 1054, such that the VMAT arc 1030 is divided into three sub-arcs 1030-1, 1030-2 and 1030-3. The radiation treatment plan is administered according to the following optimized treatment field trajectory: (1) the first sub-arc 1030-1 of the VMAT arc 1030 from the start spatial point 1050 to the first intermediate spatial point 1052; (2) the first IMRT field 1010 at the first spatial point 1040; (3) the second sub-arc 1030-2 of the VMAT arc 1030 from the first intermediate spatial point 1052 to the second intermediate spatial point 1054; (4) the second IMRT field 1020 at the second spatial point 1070; and (5) the third sub-arc 1030-3 of the VMAT arc 1030 from the second intermediate spatial point 1054 to the end spatial point 1060.

The treatment field trajectory in this example involves four beam-off transitions: the transition from the first intermediate spatial point 1052 to the first spatial point 1040 of the first IMRT field 1010; the transition from the first spatial point 1040 back to the first intermediate spatial point 1052; the transition from the second intermediate spatial point 1054 to the second spatial point 1070 of the second IMRT field 1020; and the transition from the second spatial point 1070 back to the second intermediate spatial point 1054. According to an embodiment, the intermediate spatial points 1052 and 1054 where the VMAT arc 1030 are cut are chosen such that total beam-off transition time is optimized. For example, the intermediate spatial point 1052 may be chosen such that the travel distances of the treatment axes of the treatment system from the first intermediate spatial point 1052 to the first spatial point 1040 is minimized. Similarly, the second intermediate spatial point 1054 may be chosen such that the travel distances of the treatment axes of the treatment system from the second intermediate spatial point 1054 (or an intermediate spatial point in the vicinity of the second intermediate spatial point 1054) to the second spatial point 1070 is minimized. Compared to the treatment field trajectories illustrated in FIGS. 7 and 8, this treatment field trajectory may afford a shorter total treatment time.

Figure 11:
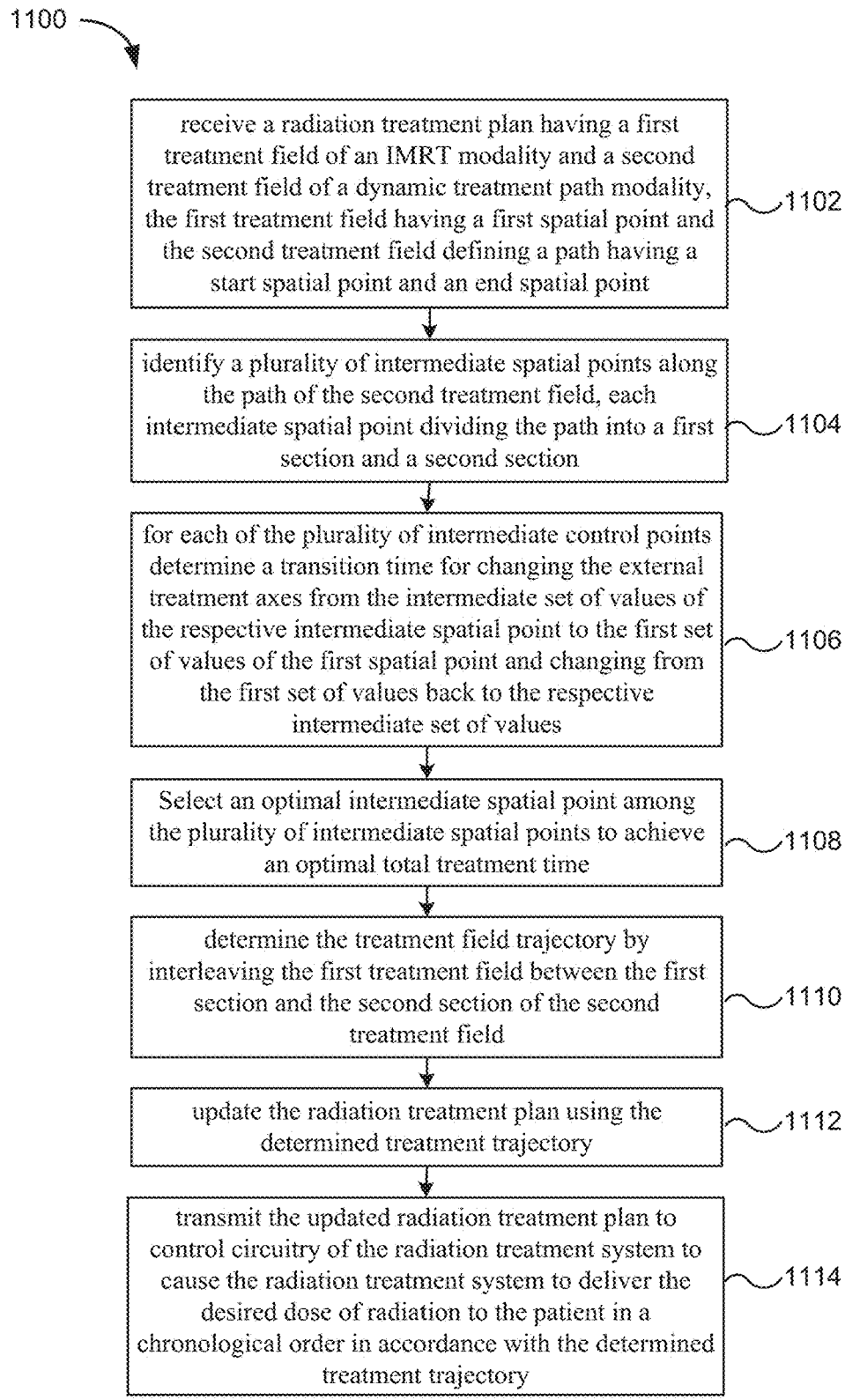
FIG. 11 is a simplified flowchart of a method of determining a treatment field trajectory according to another embodiment of the present invention.

FIG. 11 is a simplified flowchart of a method 1100 of determining a treatment field trajectory for delivering a desired dose of radiation to a treatment volume within a patient using an external-beam radiation treatment system according to embodiments of the present invention. Method 1100 can be performed wholly or partially with a computer system, as can other method described herein.

At 1102, a radiation treatment plan is received. The radiation treatment plan has a first treatment field of an IMRT modality and a second treatment field of a dynamic treatment path modality. The first treatment field has a first spatial point associated with a first set of values for treatment axes of the radiation treatment system, and the second treatment field defines a path having a start spatial point associated with a start set of values for the treatment axes and an end spatial point associated with an end set of values for the treatment axes. For example, the first spatial point of the first treatment field may define a first gantry angle for administering an IMRT field, and the start spatial point and the end spatial point of the second treatment field may define a start gantry angle and an end gantry angle of a VMAT arc. The first spatial point of the first treatment field may or may not lie on the plane of the path of the second treatment field according to various embodiments.

At 1104, a plurality of intermediate spatial points along the path of the second treatment field are identified. Each intermediate spatial point divides the path into a first section and a second section. Each intermediate spatial point is associated with a respective intermediate set of values for the treatment axes.

At 1106, a transition time for changing the treatment axes from the respective intermediate set of values to the first set of values of the first spatial point and changing from the first set of values back to the respective intermediate set of values is determined for each of the plurality of intermediate spatial points.

At 1108, an optimal intermediate spatial point is selected among the plurality of intermediate spatial points to achieve an optimal total treatment time. The optimal total treatment time includes the transition time and beam-on time for administering the first treatment field, and the first section and the second section of the second treatment field. According to various embodiments, the optimal total treatment time may be a global minimum or a local minimum compared to the total treatment times corresponding to other intermediate spatial points. In some embodiments, the optimal intermediate spatial point may be the start spatial point or the end spatial point of the second treatment field.

At 1110, the treatment field trajectory is determined by interleaving the first treatment field between the first section and the second section of the second treatment field.

In one embodiment, the treatment field trajectory may define the sequence of spatial points as follows: (1) move the treatment axes to the start spatial point; (2) administer the first section of the second treatment field from the start spatial point to the optimal intermediate spatial point; (3) move the treatment axes to the first spatial point; (4) administer the first treatment field at the first spatial point; (4) move the treatment axes to the optimal intermediate spatial point; and (5) administer the second section of the second treatment field from the optimal intermediate spatial point to the end spatial point.

It should be appreciated that the optimal intermediate spatial point may correspond to a first intermediate control point and a second intermediate control point. The first intermediate control point includes the spatial information associated with the optimal intermediate spatial point and the MU count at the end of the first section of the second treatment field. The second intermediate control point includes the spatial information associated with the optimal intermediate spatial point and the MU count at the start of the second section of the second treatment field. The same applies to the discussion below.

In another embodiment, the treatment field trajectory may define the sequence of spatial points as follows: (1) move the treatment axes to the optimal intermediate spatial point; (2) move to the first spatial point; (3) administer the first treatment field at the first spatial point; (4) move to the optimal intermediate spatial point; (5) move to the start spatial point; and (6) administer the second treatment field from the start spatial point to the end spatial point. Step (1) may be necessary to accommodate possible clinical start constraint. Step (4) may not be necessary if the first spatial point of the first treatment field is the same as the start spatial point of the second treatment field.

In a further embodiment, the treatment field trajectory may define the sequence of spatial points as follows: (1) move the treatment axes to the start spatial point of the second treatment field; (2) administer the second treatment field from the start spatial point to the end spatial point; (3) move to the optimal intermediate spatial point; (4) move to the first spatial point; (5) administer the first treatment field; and (6) move to the optimal intermediate spatial point. Step (6) may be necessary to accommodate possible clinical end constraint. Step (4) may not be necessary if the first spatial point of the first treatment field is the same as the end spatial point of the second treatment field.

In yet another embodiment, the treatment field trajectory may define the sequence of spatial points as follows: (1) move to the end spatial point of the second treatment field; (2) administer the second section of the second treatment field from the end spatial point to the optimal intermediate spatial point; (3) move to the first spatial point; (4) administer the first treatment field; (6) move to the optimal intermediate spatial point; and (7) administer the first section of the second treatment field from the optimal intermediate spatial point to the start spatial point.

At 1112, the radiation treatment plan is updated using the determined treatment field trajectory.

At 1114, the updated radiation treatment plan is transmitted to control circuitry of the radiation treatment system to cause the radiation treatment system to deliver the desired dose of radiation to the patient in a chronological order in accordance with the determined treatment field trajectory. The control circuitry sends control signals to various components of the radiation treatment system to control the movements of the treatment axes, such as the isocenter location, gantry angle, couch angles, couch offsets in accordance of the sequence of spatial points specified by the determined treatment field trajectory.

IV. Optimization of Treatment Plans Using Treatment Time Constraint

The total treatment time of a radiation treatment plan includes both beam-on time and beam-off time. The beam-on time may depend on factors such as the prescribed dose, the size of the planned target volume (PTV), the dose rate of the radiation machine, the maximum speed of the MLC leaves, and in the case of arc therapy the maximum gantry rotation speed. The beam-on time may also depend on the amount of beam modulation required for a desired dosimetric quality of a radiation treatment plan. There is usually a trade-off between the amount of MUs and the dosimetric quality of a radiation treatment plan. In general, increased modulation results in increased dosimetric quality, but it may also results in increased MUs. An increase of total MUs would lead to an increase in treatment time, because treatment machines usually have either a constant dose rate (in terms of MUs per unit time) or an upper limit for the dose rate.

This relationship is particularly important when optimizing a radiation treatment plan that includes complex combinations of multiple treatment modalities, such as combinations of IMRT fields and dynamic treatment path fields. Often, the treatment field arrangement is selected based on the need to fit the treatment into certain time slot in the treatment machine. For traditional treatment machines, VMAT fields have significantly less treatment times compared to IMRT fields. However, if future treatment machines can achieve gantry speeds comparable to MLC leaf speeds, controlling treatment times of IMRT fields may become more important.

External-beam radiation treatment plans are often created using optimization processes where a cost function is minimized. The cost function usually includes terms that depend on dosimetric aspects of a radiation treatment plan, such as dose-volume-histograms (DVHs) or dose distribution in general. The total MU count of a radiation treatment plan is often not included in the cost function. One reason for this choice is that, although in general increased modulation results in increased plan dosimetric quality, the relationship is highly non-linear and different oncologist might value the reduction in MU count differently.

Embodiments of the present invention provide optimization algorithms that takes the total MU count of a radiation treatment plan into account. According to an embodiment, a planner may specify a maximum treatment time. An optimization algorithm converts the specified maximum treatment time to a maximum total MU count, and the maximum total MU count is then used as a constraint in the optimization process.

The conversion from the specified maximum treatment time to a maximum total MU count depends on a number of factors, which may include: the selected dose rate of the radiation machine, absolute calibration of the radiation machine, maximum speed limits of various treatment axes, and the selected treatment fields and the associated field geometries. Other factors, such as time for patient imaging and positioning, may also be considered. The maximum speed limits of the treatment axes affect how fast the radiation beam may be modulated, while the maximum speed limits of the treatment axes affect the transition times between different fields. The field geometries affects the MU count, because more fields in general produces more modulation, which in turn requires more MUs. There are also more complex effects. For example, the "sliding window" technique of IMRT requires MLC leaf movement during delivery of the IMRT field, which causes more MUs since MLC leaf movement takes a finite time. If the number of fields is increased, the transition times between the fields may be increased, since the total travel distances of the treatment axes are increased.

According to an embodiment, a cost function for the optimization algorithm includes a term that penalizes any violation of the upper constraint for the MU count. For example, the cost function may include a term that is proportional to the square of the total MU count of a radiation treatment plan in excess of the maximum total MU count. In other embodiments, the cost function term may be of other functions of the total MU count of a radiation treatment plan in excess of the maximum total MU count. For example, it could be a polynomial function of an order greater than two, or it could be an exponential function.

According to some embodiments, to lower the MU count, the algorithm may require more fluence smoothing by assigning a stronger smoothing constraint.

Figure 12:
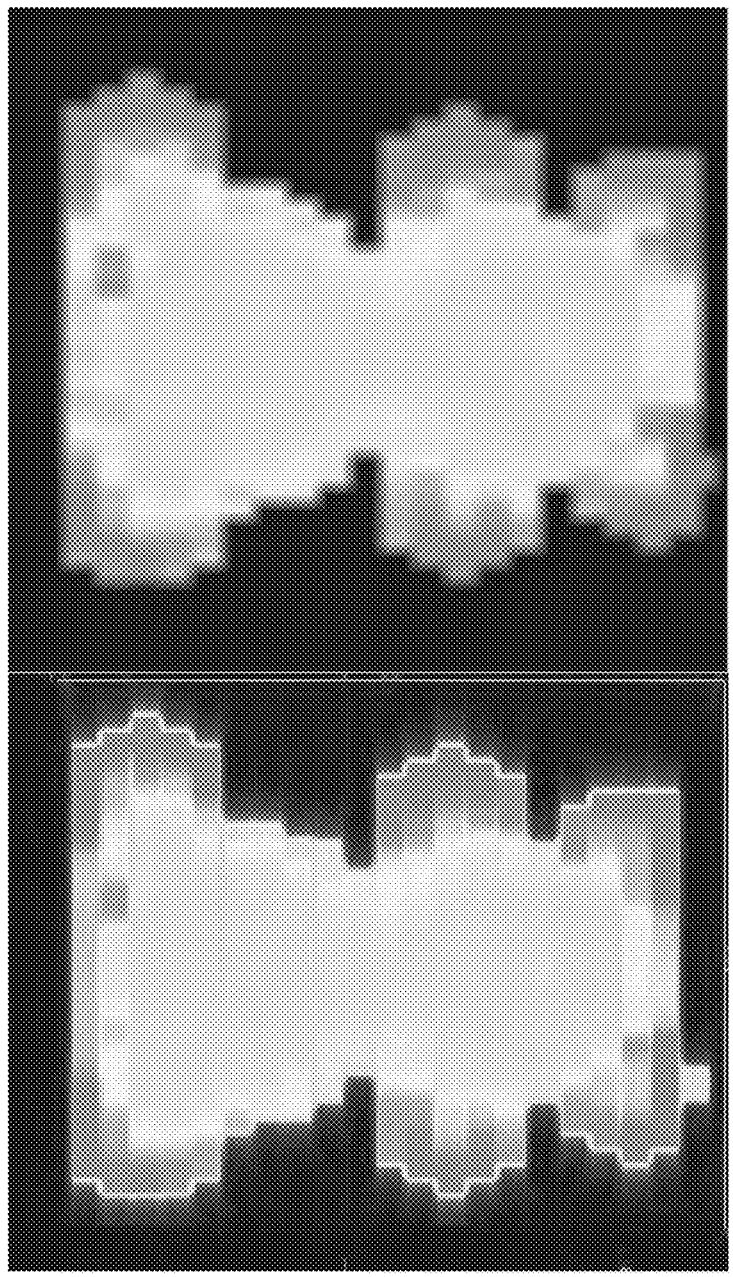
FIG. 12 shows (a) an example fluence map that includes some high frequency noise; and (b) an example fluence map where the high frequency noise shown in FIG. 12(a) is removed by fluence smoothing.

FIG. 12 shows (a) an example fluence map that includes some high frequency noise; and (b) another example fluence map where the high frequency noise shown in FIG. 12(a) is removed by fluence smoothing. A smoother fluence would require less modulation; less modulation means a larger aperture size defined by the MLCs; and larger aperture size means less amount of MUs are needed to deliver a given amount of dose. Here, the aperture is understood to be the aggregate opening over time as defined by the MLC. Typically, the larger the amount of modulation over time in the size of the aperture means that the shape of the aperture changes significantly over the course of the treatment. This would lead to longer treatment time, since changing the MLC leaf positions takes time. Assigning the amount of fluence smoothing is always a trade-off. If too little smoothing, fluence is too noisy, which would increase MU count and decrease deliverability of the plan. On the other hand, too much smoothing may affect dose gradient and results in a slower dose fall-off to normal tissues. This may in turn affect the plan quality, as it may results in larger dose to OARs.

Figure 13:
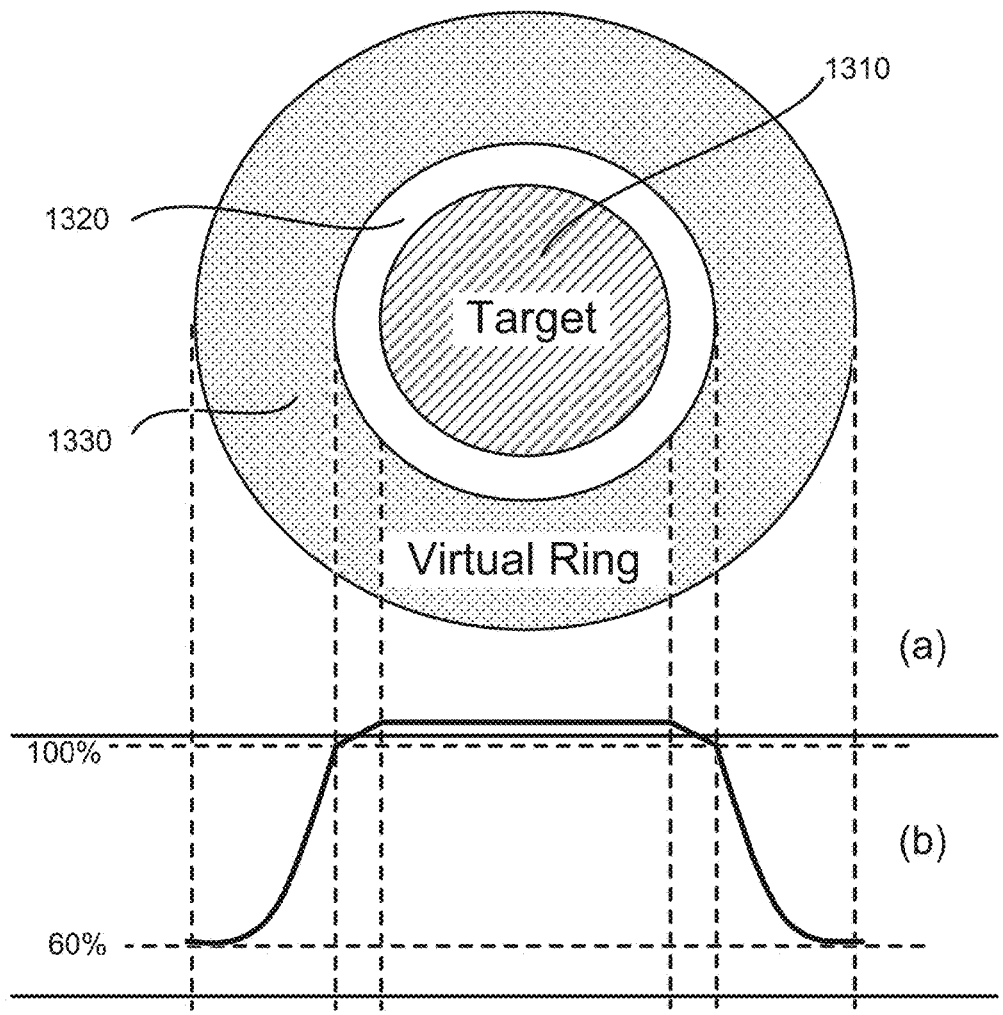
FIG. 13 illustrates (a) a schematic "virtual ring" of healthy tissue surrounding a target volume; and (b) a cross-section of an example dose distribution.

FIG. 13 illustrates (a) a schematic virtual "ring" of healthy tissue 1330 surrounding a target volume 1310; and (b) a cross-section of an example dose distribution. The dose distribution is substantially homogeneous within the target volume 1310, and falls off to 100% in the intermediate region 1320, and further falls off to 60% in the virtual ring of healthy tissue 1330. More fluence smoothing may lead to a more gradual fall-off, resulting in a larger virtual ring 1330; a larger virtual ring 1330 may lead to more dose spillage to nearby organ at risk (OAR).

According to an embodiment, in each iteration loop, an MLC leaf sequence is generated. The total MU count needed to deliver a dose corresponding to the MLC leaf sequence is then calculated for the evaluation of the cost function. According to other embodiments, the total MU count (or an upper bound of it) may be determined by other means before the full leaf sequence is done.

Figure 14:
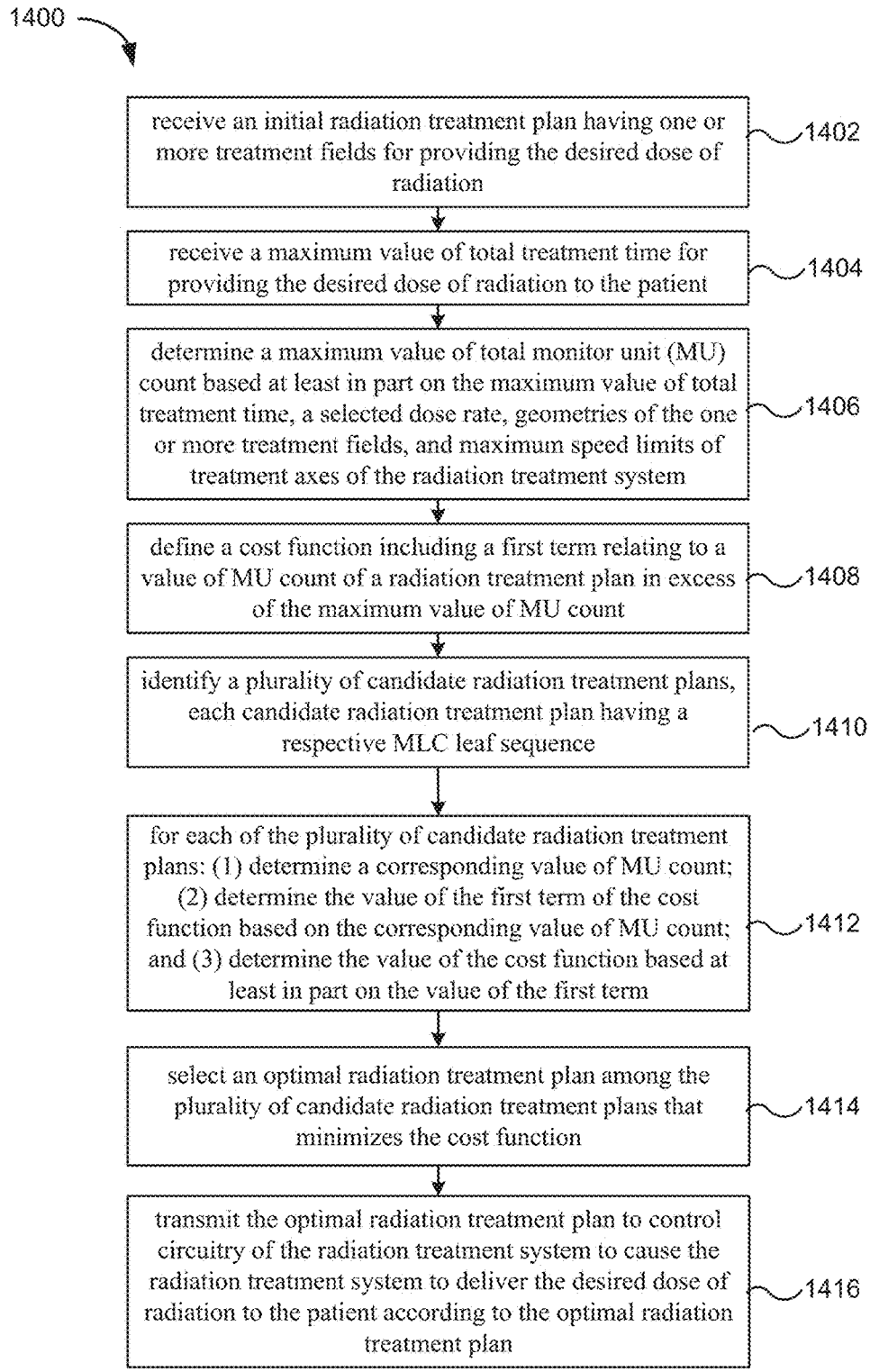
FIG. 14 is a simplified flowchart of a method of developing a radiation treatment plan according to an embodiment of the present invention.

FIG. 14 is a simplified flowchart of a method 1400 of determining a radiation treatment plan for delivering a desired dose of radiation to a treatment volume within a patient using an external-beam radiation treatment system according to embodiments of the present invention. Method 1400 can be performed wholly or partially with a computer system.

At 1402, an initial radiation treatment plan is received. The initial radiation treatment plan includes one or more treatment fields for providing the desired dose of radiation. For example, the initial radiation treatment plan may be obtained by using one of the treatment planning algorithms available.

At 1404, a maximum value of total treatment time for providing the desired dose of radiation to the patient is received. The maximum value of total treatment time is an input to the optimization algorithm and is specified by a planner.

At 1406, a maximum value of total monitor unit (MU) count is determined based at least in part on the maximum value of total treatment time, a selected dose rate, geometries of the one or more treatment fields, and maximum speed limits of treatment axes of the radiation treatment system. In some embodiments, determining the maximum value of total MU count may also be based on absolute calibration of the radiation machine and time for patient imaging and positioning.

At 1408, a cost function including a first term is defined. The first term relates to a value of MU count of a radiation treatment plan in excess of the maximum value of MU count. In one embodiment, the cost function may include a term that is proportional to the square of the the total MU count of a radiation treatment plan in excess of the maximum total MU count. In other embodiments, the cost function term may be of other functions of the total MU count of a radiation treatment plan in excess of the maximum total MU count. For example, it could be a polynomial function of an order greater than two, or it could be an exponential function.

At 1410, a plurality of candidate radiation treatment plans is identified. Each candidate radiation treatment plan has a respective MLC leaf sequence. In some embodiments, the respective MLC leaf sequence of each candidate radiation treatment plan may correspond to a given smoothing constraint.

At 1412, for each of the plurality of candidate radiation treatment plans, (1) a corresponding value of MU count is determined based on the respective MLC leaf sequence; (2) the value of the first term of the cost function is determined based on the corresponding value of MU count; and (3) the value of the cost function is determined based at least in part on the value of the first term.

At 1414, an optimal radiation treatment plan is selected among the plurality of candidate radiation treatment plans. In one embodiment, the optimal radiation treatment plan minimizes the cost function. In general, the optimal radiation treatment plan would meet the maximum value of total MU count.

At 1416, the optimal radiation treatment plan is transmitted to control circuitry of the radiation treatment system. The control circuitry sends control signals to various components of the radiation treatment system to cause the radiation treatment system to deliver the desired dose of radiation to the patient according to the optimal radiation treatment plan.

According to an embodiment, identifying the plurality of candidate radiation treatment plans includes determining a respective treatment field trajectory for each of the plurality of candidate radiation treatment plans to minimize total treatment time, as discussed in Section III above.

In another embodiment, a soft term may be added to the cost function that would suppress the total MU count with lesser weight even if the upper constraint for the total MU count is met. For example, the cost function may include a term that is proportional to the total MU count of a radiation treatment plan in excess of the maximum total MU count with a first weight, and proportional to the total MU count when the total MU count is less than the maximum MU count with a second weight less than the first weight. Such optimization would result in an optimal radiation treatment plan that does not use an excessive amount of MUs.

In an alternative embodiment, a user may define multiple different time constraints, which are converted to multiple different MU constraints. The optimization algorithm imposes penalty with increasing weight for increasing time. For example, the multiple different MU constraints may include a first MU count and a second MU count, the second MU count being less than the first MU count. The cost function may include a term that is proportional to an MU count of a radiation treatment plan in excess of the first MU count with a first weight; and is proportional to an MU count of a radiation treatment plan in excess of the second MU count with a second weight, where the second weight is less than the first weight.

In some embodiments, the optimization algorithm may make decisions regarding selections of different treatment fields and number of fields, e.g., IMRT fields and dynamic treatment path fields, according to how different treatment fields fit within the given time constraint. During the optimization process, multiple plan candidates using different field geometries may be evaluated. Since different field geometries might have different trade-offs between plan quality and required treatment time, the optimization algorithm considers which field geometry provides the best plan quality in the given time constraint. In one embodiment, the algorithm evaluates each candidate with the same time constraint and selects the plan that has the best plan quality. In another embodiment, the algorithm evaluates each candidate without time constraint and selects the most promising field geometry in terms of plan quality based on the required treatment time.

V. Imaging Dose Optimization

Imaging techniques are becoming available for modern radiation treatment systems. They are routinely used for several purposes, such as patient positioning, checking tumor response to treatment and changes in patient tissue during the treatment course, and on-line treatment plan verification. All these radiation-based imaging techniques are typically by design low-dose techniques. However, due to possibly large number of images over the treatment course and the concern over the long term effects on exposure of healthy tissues to low-dose radiation, it is of interest to limit, model and take into account in a treatment plan even small dose of radiation to healthy tissues.

According to embodiments of the invention, the imaging setup is optimized such that the resulting imaging dose will add up to the treatment dose in an optimal way, thereby maximizing the healthy tissue sparing. In one embodiment, imaging setup is optimized separately from the treatment plan optimization, and the resulting imaging dose is used as the base dose when optimizing the treatment dose distribution. For example, assume that a treatment plan includes 20 fractions, and an image will be acquired before the delivery of each treatment fraction. The imaging parameters for the 20 imaging sessions may be optimized such that imaging quality goals may be achieved while having the least cumulative radiation dose. The cumulative radiation dose may then be used as a base radiation dose when optimizing the treatment dose distribution. Imaging parameters that may be varied in the optimization may include, for example, imaging directions, energy of the radiation beam used for imaging, and imaging exposure times. In the case of cone beam computed tomography (CBCT), imaging parameters may also include the size of the imaging field, which is determined by the opening of the jaws in the beam source. The optimization constraints may include imaging quality, cumulative radiation dose, and volumetric dose distribution constraints similar to those used when optimizing a treatment plan.

In an alternative embodiment, imaging setup is optimized together with the treatment plan optimization in order to achieve an optimal total dose distribution. In this case, imaging parameters, such as imaging directions, imaging exposure times, and/or size of imaging field, may be varied together with other treatment variables, such as MLC leaf sequence, in order to achieve an optimal overall dose distribution. The treatment plan can be optimized either offline or online based on the decision taken in the treatment room.

In another embodiment, an optimization algorithm involves optimizing imaging dose distribution for each imaging session such that the sum of these imaging doses would be more optimal compared to a sum of the doses from the same amount of mutually identical imaging sessions.

According to an embodiment, in the optimization of treatment plans using treatment time constraint discussed in Section IV above, the initial radiation treatment plan includes one or more imaging sessions, and each of the plurality of candidate radiation treatment plans includes a respective imaging setup for performing the one or more imaging sessions. The corresponding value of MU count for each of the plurality of candidate radiation treatment plans includes the MU count for performing the one or more imaging sessions.

According to some embodiments, in the optimization of treatment trajectories of a radiation treatment plan discussed in Section III above, one or more imaging sessions may be programed into the treatment field trajectory by interleaving and intermixing the plurality of treatment fields with the one or more imaging sessions. In one embodiment, the imaging geometries of the one or more imaging sessions, such as the imaging directions, may be optimized together with the optimization of treatment trajectories.

Figure 15:
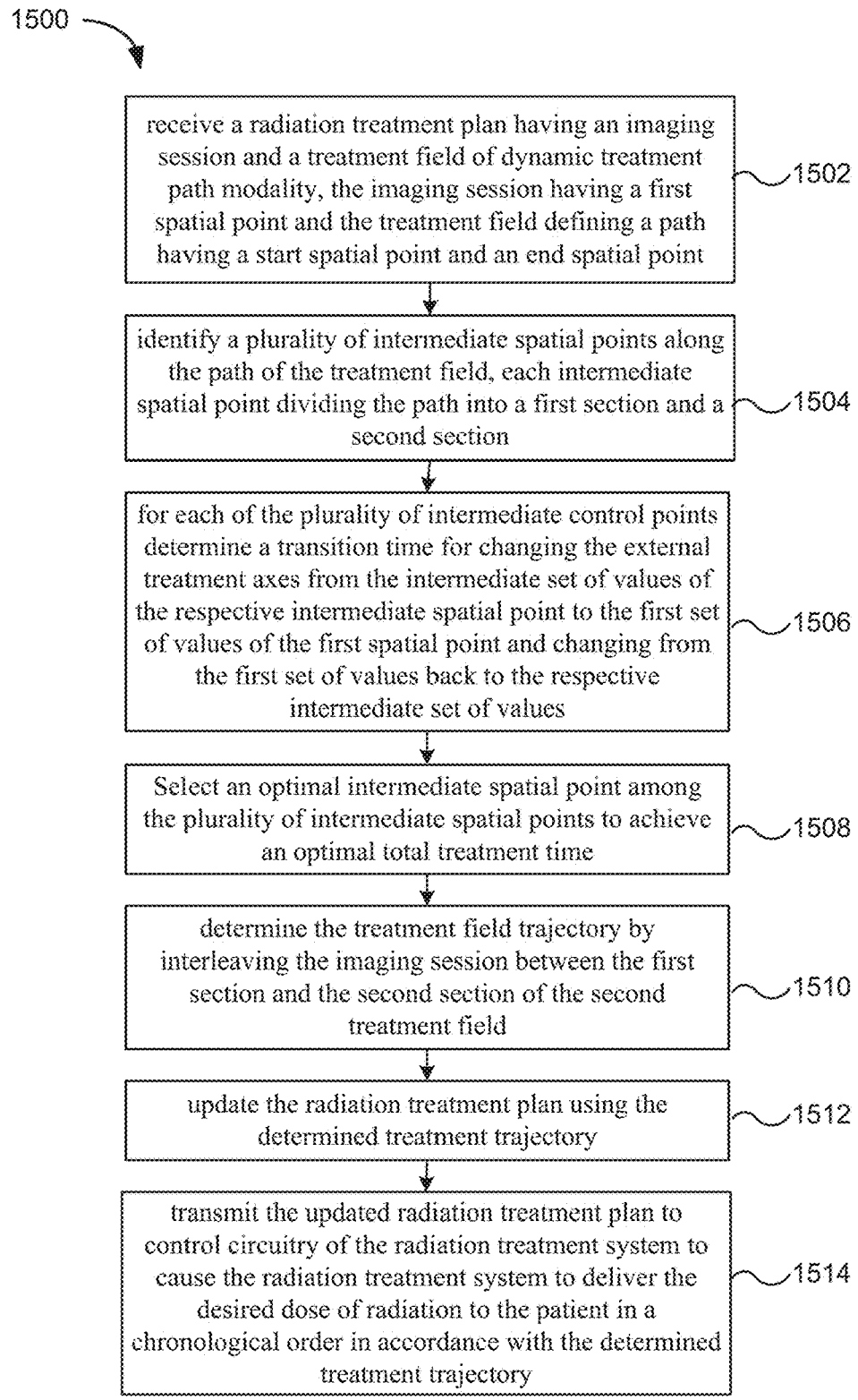
FIG. 15 is a simplified flowchart of a method of determining a treatment field trajectory of a radiation treatment plan including an imaging session according to an embodiment of the present invention.

FIG. 15 is a simplified flowchart of a method 1500 of determining a treatment field trajectory of a radiation treatment plan including an imaging session according to an embodiment of the present invention.

At 1502, a radiation treatment plan is received. The radiation treatment plan includes an imaging session and a treatment field of a dynamic treatment path modality. The imaging session has a first spatial point associated with a first set of values for the treatment axes of the radiation treatment system. The treatment field defines a path having a start spatial point and an end spatial point, the start spatial point associated with a start set of values for the treatment axes, and the end spatial point associated with an end set of values for the treatment axes.

At 1504, a plurality of intermediate spatial points along the path of the treatment field is identified. Each intermediate spatial point divides the path into a first section and a second section, and is associated with a respective intermediate set of values for the treatment axes.

At 1506, for each of the plurality of intermediate spatial points, a transition time for changing the treatment axes from the intermediate set of values of the respective intermediate spatial point to the first set of values of the first spatial point and changing from the first set of values back to the respective intermediate set of values is determined.

At 1508, an optimal intermediate spatial point is selected among the plurality of intermediate spatial points to achieve an optimal total treatment time. The optimal total treatment time includes the transition time and beam-on time for administering the first section and the second section of the treatment field. According to various embodiments, the optimal total treatment time may be a global minimum or a local minimum compared to the total treatment times corresponding to other intermediate spatial points.

At 1510, the treatment field trajectory is determined by interleaving the imaging session between the first section and the second section of the second treatment field. In one embodiment, the treatment field trajectory may define the sequence of spatial points as follows: (1) from the start spatial point to the optimal intermediate spatial point, (2) from the optimal intermediate spatial point to the first spatial point, (3) from the first spatial point back to the optimal intermediate spatial point, and (4) from the optimal intermediate spatial point to the end spatial point. In another embodiment, the treatment field trajectory may define the sequence of spatial points as follows: (1) from the end spatial point to the optimal intermediate spatial point, (2) from the optimal intermediate spatial point to the first spatial point, (3) from the first spatial point back to the optimal intermediate spatial point, and (4) from the optimal intermediate spatial point to the start spatial point.

At 1512, the radiation treatment plan is updated using the determined treatment trajectory. In one embodiment, the updated radiation treatment plan specifies the order of the delivering the treatment field and performing the imaging as follows: (1) the first section of the treatment field, (2) the imaging, and (3) the second section of the treatment field. In another embodiment, the updated radiation treatment plan specifies the order delivering the treatment field and performing the imaging as follows: (1) the second section of the treatment field, (2) the imaging, and (3) the first section of the treatment field.

At 1514, the updated radiation treatment plan is transmitted to control circuitry of the radiation treatment system. The control circuitry sends control signals to various components of the radiation treatment system to cause the radiation treatment system to deliver the desired dose of radiation to the patient in a chronological order in accordance with the determined treatment trajectory.

It should be appreciated that the specific steps illustrated in FIGS. 9, 11, 14, and 15 provide particular methods according to an embodiment of the present invention. For each of the methods, other sequences of steps may also be performed according to alternative embodiments. For example, alternative embodiments of the present invention may perform the steps in a different order. Moreover, the individual steps may include multiple sub-steps that may be performed in various sequences as appropriate to the individual step. Furthermore, additional steps may be added and some steps may be removed depending on the particular applications. One of ordinary skill in the art would recognize many variations, modifications, and alternatives.

VI. Computer System

Figure 16:
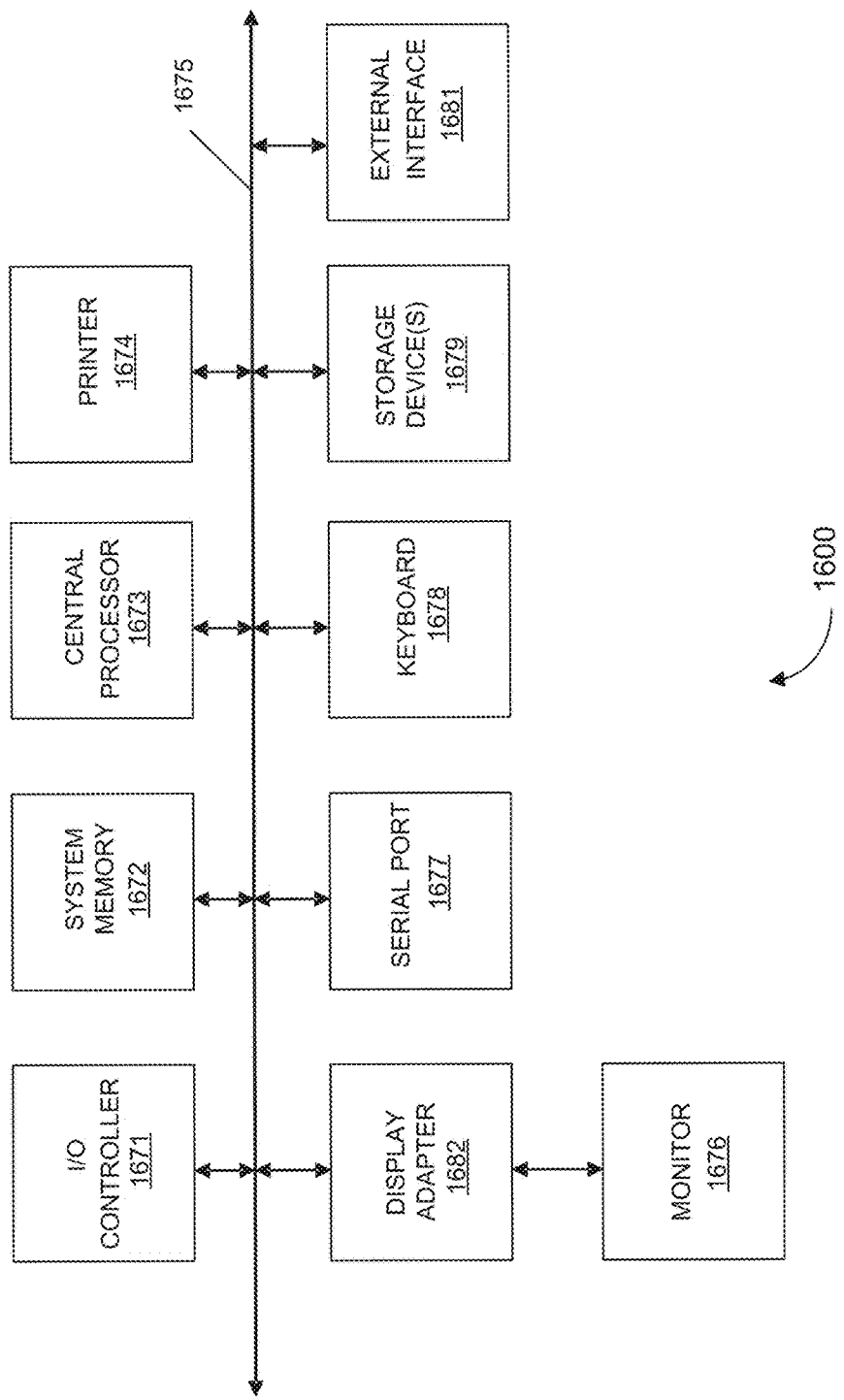
FIG. 16 shows a block diagram of an example computer system usable with system and methods according to embodiments of the present invention.

Any of the computer systems mentioned herein may utilize any suitable number of subsystems. Examples of such subsystems are shown in FIG. 16 in computer system 1600. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 16 are interconnected via a system bus 1675. Additional subsystems such as a printer 1674, keyboard 1678, storage device(s) 1679, monitor 1676, which is coupled to display adapter 1682, and others are shown. Peripherals and input/output (I/O) devices, which couple to I/O controller 1671, can be connected to the computer system by any number of means known in the art, such as serial port 1677. For example, serial port 1677 or external interface 1681 (e.g. Ethernet, Wi-Fi, etc.) can be used to connect computer system 1600 to a wide area network such as the Internet, a mouse input device, or a scanner. The interconnection via system bus 1675 allows the central processor 1673 to communicate with each subsystem and to control the execution of instructions from system memory 1672 or the storage device(s) 1679 (e.g., a fixed disk, such as a hard drive or optical disk), as well as the exchange of information between subsystems. The system memory 1672 and/or the storage device(s) 1679 may embody a computer readable medium. Any of the data mentioned herein can be output from one component to another component and can be output to the user.

A computer system can include a plurality of the same components or subsystems, e.g., connected together by external interface 1681 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned here are incorporated by reference in their entirety for all purposes. None is admitted to be prior art.

What is claimed is:

1. A computer-implemented method of determining a treatment field trajectory for delivering a desired dose of radiation to a treatment target within a patient using an external-beam radiation treatment system, the method comprising:

receiving a radiation treatment plan having a first treatment field of an intensity modulated radiation therapy (IMRT) modality and a second treatment field of a dynamic treatment path modality, the first treatment field having a first spatial point associated with a first set of values for treatment axes of the radiation treatment system, and the second treatment field defining a treatment path having a start spatial point associated with a start set of values for the treatment axes and an end spatial point associated with an end set of values for the treatment axes;

identifying, using a computer system, a plurality of intermediate spatial points along the treatment path of the second treatment field, each intermediate spatial point dividing the treatment path into a first section and a second section, and each intermediate spatial point associated with a respective intermediate set of values for the treatment axes;

for each of the plurality of intermediate spatial points:
determining, using the computer system, a transition time for changing the treatment axes from the respective intermediate set of values to the first set of values of the first spatial point and changing from the first set of values back to the respective intermediate set of values;

selecting, using the computer system, an optimal intermediate spatial point among the plurality of intermediate spatial points to achieve an optimal total treatment time, the optimal total treatment time including the transition time and beam-on time for administering the first treatment field and the second treatment field;

determining the treatment field trajectory by interleaving the first treatment field between the first section and the second section of the second treatment field; and updating the radiation treatment plan using the determined treatment field trajectory, wherein the radiation treatment plan is to be used by the external-beam radiation treatment system for delivering the desired dose of radiation.

2. The method of claim 1, further comprising transmitting the updated radiation treatment plan to control circuitry of the radiation treatment system to cause the radiation treatment system to deliver the desired dose of radiation to the patient in a chronological order in accordance with the determined treatment field trajectory.

3. The method of claim 1, wherein the first spatial point of the first treatment field is not on the treatment path of the second treatment field.

4. The method of claim 1, wherein delivering the desired dose of radiation includes:
moving the treatment axes to the start spatial point;
administering the first section of the second treatment field from the start spatial point to the optimal intermediate spatial point;
moving the treatment axes to the first spatial point;
administering the first treatment field at the first spatial point;
moving the treatment axes to the optimal intermediate spatial point; and
administering the second section of the second treatment field from the optimal intermediate spatial point to the end spatial point.

5. The method of claim 4, wherein:
the optimal intermediate spatial point corresponds to a first intermediate control point and a second intermediate control point;

administering the first section of the second treatment field from the start spatial point to the optimal intermediate spatial point comprises administering the first section of the second treatment field from a start control point corresponding to the start spatial point to the first intermediate control point; and administering the second section of the second treatment field from the optimal intermediate spatial point to the end spatial point comprises administering the second section of the second treatment field from the second intermediate control point to an end control point corresponding to the end spatial point.

6. The method of claim 1, wherein delivering the desired dose of radiation includes:
moving the treatment axes to the optimal intermediate spatial point;
moving the treatment axes to the first spatial point;
administering the first treatment field at the first spatial point;
moving the treatment axes to the optimal intermediate spatial point;
moving the treatment axes to the start spatial point; and
administering the second treatment field from the start spatial point to the end spatial point.

7. The method of claim 1, wherein delivering the desired dose of radiation includes:
moving the treatment axes to the start spatial point;
administering the second treatment field from the start spatial point to the end spatial point;
moving the treatment axes to the optimal intermediate spatial point;
moving the treatment axes to the first spatial point;
administering the first treatment field at the first spatial point; and
moving the treatment axes to the optimal intermediate spatial point.

8. The method of claim 1, wherein delivering the desired dose of radiation includes:
moving the treatment axes to the end spatial point;
administering the second section of the second treatment field from the end spatial point to the optimal intermediate spatial point;
moving the treatment axes to the first spatial point;
administering the first treatment field at the first spatial point;
moving the treatment axes to the optimal intermediate spatial point; and
administering the first section of the second treatment field from the optimal intermediate spatial point to the start spatial point.

9. The method of claim 1, wherein the radiation treatment plan further includes a third treatment field of either the IMRT modality or the dynamic treatment path modality, and determining the treatment field trajectory further comprises:
determining an optimal chronological order of administering the first treatment field, the first section and the second section of the second treatment field, and the third treatment field to achieve the optimal total treatment time.

10. The method of claim 1, wherein the dynamic treatment path modality comprises volumetric modulated arc therapy (VMAT).

11. The method of claim 1, wherein the IMRT modality comprises a static IMRT modality where leaves of a multileaf collimator (MLC) do not move while radiation dose is being delivered.

12. The method of claim 1, wherein the IMRT modality comprises a dynamic IMRT modality where leaves of a multileaf collimator (MLC) move while radiation dose is being delivered.

13. A computer product comprising a non-transitory computer readable medium storing a plurality of instructions that when executed control a computer system to determine a treatment field trajectory for delivering a desired dose of radiation to a treatment target within a patient using an external-beam radiation treatment system, the instructions comprising:
receiving a radiation treatment plan having a first treatment field of an intensity modulated radiation therapy (IMRT) modality and a second treatment field of a dynamic treatment path modality, the first treatment field having a first spatial point associated with a first set of values for treatment axes of the radiation treatment system, and the second treatment field defining a treatment path having a start spatial point associated with a start set of values for the treatment axes and an end spatial point associated with an end set of values for the treatment axes;
identifying, using the computer system, a plurality of intermediate spatial points along the treatment path of the second treatment field, each intermediate spatial point dividing the treatment path into a first section and a second section, and each intermediate spatial point associated with a respective intermediate set of values for the treatment axes;
for each of the plurality of intermediate spatial points:
determining, using the computer system, a transition time for changing the treatment axes from the respective intermediate set of values to the first set of values of the first spatial point and changing from the first set of values back to the respective intermediate set of values;
selecting, using the computer system, an optimal intermediate spatial point among the plurality of intermediate spatial points to achieve an optimal total treatment time, the optimal total treatment time including the transition time and beam-on time for administering the first treatment field and the second treatment field;
determining the treatment field trajectory by interleaving the first treatment field between the first section and the second section of the second treatment field; and
updating the radiation treatment plan using the determined treatment field trajectory, wherein the radiation treatment plan is to be used by the external-beam radiation treatment system for delivering the desired dose of radiation.

14. The computer product of claim 13, wherein the instructions further comprise:
transmitting the updated radiation treatment plan to control circuitry of the radiation treatment system to cause the radiation treatment system to deliver the desired dose of radiation to the patient in a chronological order in accordance with the determined treatment field trajectory.

15. The computer product of claim 13, wherein the first spatial point of the first treatment field is not on the treatment path of the second treatment field.

16. The computer product of claim 13, wherein delivering the desired dose of radiation includes:
moving the treatment axes to the start spatial point;
administering the first section of the second treatment field from the start spatial point to the optimal intermediate spatial point;

moving the treatment axes to the first spatial point;
administering the first treatment field at the first spatial point;
moving the treatment axes to the optimal intermediate spatial point; and
administering the second section of the second treatment field from the optimal intermediate spatial point to the end spatial point.

17. The computer product of claim 16, wherein:
the optimal intermediate spatial point corresponds to a first intermediate control point and a second intermediate control point;
administering the first section of the second treatment field from the start spatial point to the optimal intermediate spatial point comprises administering the first section of the second treatment field from a start control point corresponding to the start spatial point to the first intermediate control point; and
administering the second section of the second treatment field from the optimal intermediate spatial point to the end spatial point comprises administering the second section of the second treatment field from the second intermediate control point to an end control point corresponding to the end spatial point.

18. The computer product of claim 13, wherein delivering the desired dose of radiation includes:
moving the treatment axes to the optimal intermediate spatial point;
moving the treatment axes to the first spatial point;
administering the first treatment field at the first spatial point;
moving the treatment axes to the optimal intermediate spatial point;
moving the treatment axes to the start spatial point; and
administering the second treatment field from the start spatial point to the end spatial point.

19. The computer product of claim 13, wherein delivering the desired dose of radiation includes:
moving the treatment axes to the start spatial point;
administering the second treatment field from the start spatial point to the end spatial point;
moving the treatment axes to the optimal intermediate spatial point;
moving the treatment axes to the first spatial point;
administering the first treatment field at the first spatial point; and
moving the treatment axes to the optimal intermediate spatial point.

20. The computer product of claim 13, wherein delivering the desired dose of radiation includes:
moving the treatment axes to the end spatial point;
administering the second section of the second treatment field from the end spatial point to the optimal intermediate spatial point;
moving the treatment axes to the first spatial point;
administering the first treatment field at the first spatial point; moving the treatment axes to the optimal intermediate spatial point; and
administering the first section of the second treatment field from the optimal intermediate spatial point to the start spatial point.

21. The computer product of claim 13, wherein the radiation treatment plan further includes a third treatment field of either the IMRT modality or the dynamic treatment path modality, and determining the treatment field trajectory further comprises:
determining an optimal chronological order of administering the first treatment field, the first section and the second section of the second treatment field, and the third treatment field to achieve the optimal total treatment time.

22. The computer product of claim 13, wherein the dynamic treatment path modality comprises volumetric modulated arc therapy (VMAT).

23. The computer product of claim 13, wherein the IMRT modality comprises a static IMRT modality where leaves of a multileaf collimator (MLC) do not move while radiation dose is being delivered, or a dynamic IMRT modality where leaves of a multileaf collimator (MLC) move while radiation dose is being delivered.

* * * * *